(12) United States Patent
Yoshida et al.

(10) Patent No.: US 8,236,842 B2
(45) Date of Patent: *Aug. 7, 2012

(54) SALT AND PROCESS FOR PRODUCING ACID GENERATOR

(75) Inventors: Isao Yoshida, Ikeda (JP); Koji Ichikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/025,637

(22) Filed: Feb. 11, 2011

(65) Prior Publication Data

US 2011/0201823 A1 Aug. 18, 2011

(30) Foreign Application Priority Data

Feb. 16, 2010 (JP) ................................. 2010-031082
Aug. 30, 2010 (JP) ................................. 2010-191871

(51) Int. Cl.
*A61K 31/4174* (2006.01)
*C07D 233/60* (2006.01)

(52) U.S. Cl. ..................................... 514/397; 548/311.1

(58) Field of Classification Search .................. 548/397, 548/311.1; 514/311.1, 397
See application file for complete search history.

(56) References Cited

U.S. PATENT DOCUMENTS

2006/0194982 A1* 8/2006 Harada et al.

OTHER PUBLICATIONS

U.S. Appl. No. 12/985,838, commonly assigned.*

* cited by examiner

*Primary Examiner* — Kamal Saeed
*Assistant Examiner* — Janet L Coppins
(74) *Attorney, Agent, or Firm* — Birch, Stewart, Kolasch & Birch, LLP

(57) ABSTRACT

A salt represented by the formula (I0):

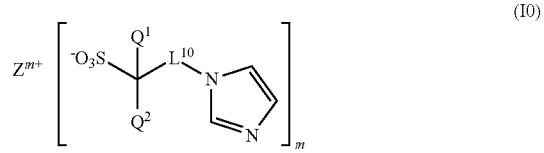

wherein $Q^1$ and $Q^2$ each independently represent a fluorine atom or a C1-C6 perfluoroalkyl group, $L^1$ represents a divalent C1-C17 hydrocarbon group in which one or more —$CH_2$— can be replaced by —O— or —CO—, m represents 1 or 2, and $Z^{m+}$ represents m-valent organic or inorganic cation.

11 Claims, No Drawings

SALT AND PROCESS FOR PRODUCING ACID GENERATOR

This nonprovisional application claims priority under 35 U.S.C. §119(a) on Patent Application No. 2010-031082 filed in JAPAN on Feb. 16, 2010 and on Patent Application No. 2010-191871 filed in JAPAN on Aug. 30, 2010, the entire contents of which are hereby incorporated by reference.

FIELD OF THE INVENTION

The present invention relates to a salt suitable for an intermediate for producing an acid generator and a process for producing an acid generator.

BACKGROUND OF THE INVENTION

A chemically amplified positive resist composition used for semiconductor microfabrication employing a lithography process contains an acid generator generating an acid by irradiation.

US 2006/0194982 A1 discloses a process for producing an acid generator represented by the formula (B1-1) which comprises reacting a salt represented by the formula (H1-5) with a salt represented by the formula (H1-4) obtained by reacting a salt represented by the formula (H1-2) with a compound represented by the formula (H1-3) as described below.

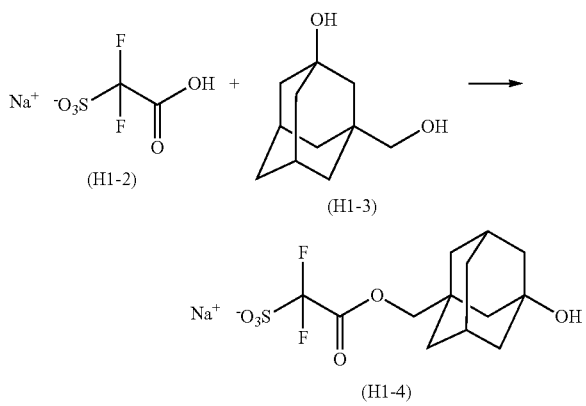

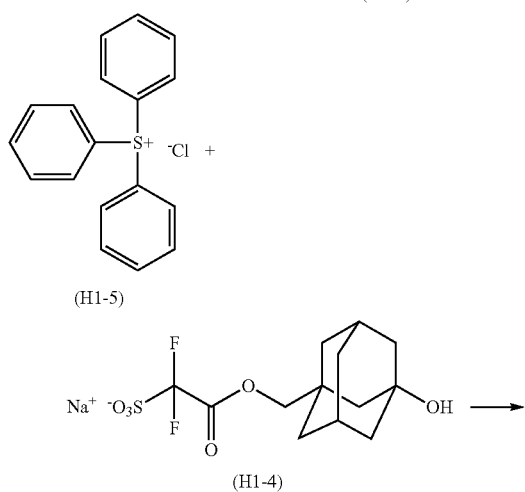

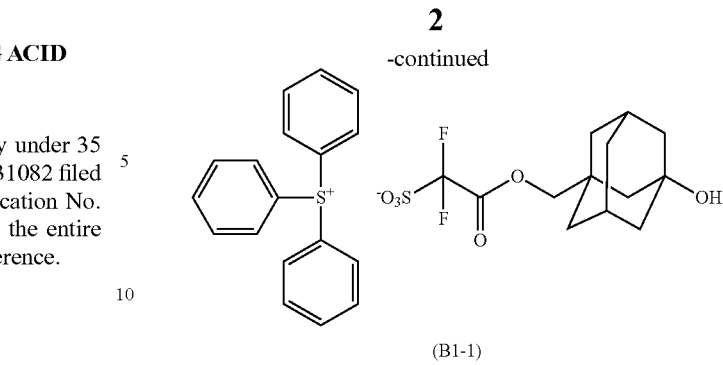

In the process disclosed in US 2006/0194982 A1, the salt represented by the formula (H1-4) is used as an intermediate for producing an acid generator.

SUMMARY OF THE INVENTION

An object of the present invention is to provide a novel salt suitable for an intermediate for producing an acid generator and a process for producing an acid generator.

The present invention relates to the followings:

<1> A salt represented by the formula (I0):

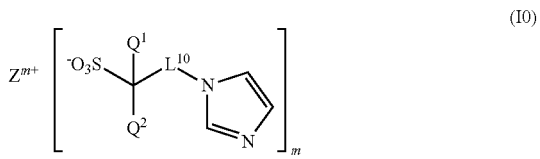

wherein $Q^1$ and $Q^2$ each independently represent a fluorine atom or a C1-C6 perfluoroalkyl group, $L^{10}$ represents a divalent C1-C17 hydrocarbon group in which one or more —$CH_2$— can be replaced by —O— or —CO—, m represents 1 or 2, and $Z^{m+}$ represents m-valent organic or inorganic cation;

<2> The salt according to <1>, wherein m is 1;

<3> The salt according to <1> or <2>, wherein $L^{10}$ is a divalent C1-C17 saturated hydrocarbon group in which one or more —$CH_2$— can be replaced by —O— or —CO—;

<4> The salt according to <1> or <2>, wherein $L^{10}$ is —CO—;

<5> The salt according to <1>, wherein the salt represented by the formula (I0) is a salt represented by the formula (I):

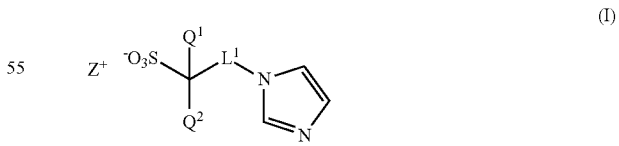

wherein $Q^1$ and $Q^2$ each independently represent a fluorine atom or a C1-C6 perfluoroalkyl group, $L^1$ represents a divalent C1-C17 saturated hydrocarbon group in which one or more —$CH_2$— can be replaced by —O— or —CO—, and $Z^+$ represents a monovalent organic or inorganic cation;

<6> The salt according to <5>, wherein $L^1$ is —CO—;

<7> The salt according to <5> or <6>, wherein $Z^+$ is a triarylsulfonium cation or an alkali metal cation;

<8> The salt according to <5> or <6>, wherein $Z^+$ is a triarylsulfonium cation;

<9> A process for producing a salt represented by the formula (I):

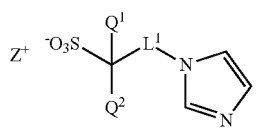

wherein $Q^1$ and $Q^2$ each independently represent a fluorine atom or a C1-C6 perfluoroalkyl group, $L^1$ represents a divalent C1-C17 saturated hydrocarbon group in which one or more —CH$_2$— can be replaced by —O— or —CO—, and $Z^+$ represents a monovalent organic or inorganic cation, which comprises reacting a salt represented by the formula (II):

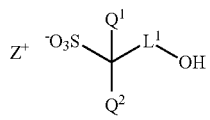

wherein $Q^1$, $Q^2$, $L^1$ and $Z^+$ are the same as defined above, with carbonyldiimidazole;

<10> A process for producing a salt represented by the formula (B1):

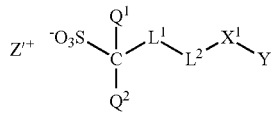

wherein $Q^1$ and $Q^2$ each independently represent a fluorine atom or a C1-C6 perfluoroalkyl group, $L^1$ represents a divalent C1-C17 saturated hydrocarbon group in which one or more —CH$_2$— can be replaced by —O— or —CO—, $L^2$ represents —O— or —HR$^3$— in which R$^3$ represents a hydrogen atom or a C1-C4 alkyl group, $X^1$ represents a single bond or a C1-C6 alkanediyl group, Y represents a C1-C18 alkyl group which can have one or more substituents or a C3-C18 saturated cyclic hydrocarbon group which can have one or more substituents and one or more —CH$_2$— in the alkyl group and the saturated cyclic hydrocarbon group can be replaced by —O—, —SO$_2$— or —CO—, and $Z'^+$ represents a monovalent organic cation, which comprises reacting a salt represented by the formula (I'):

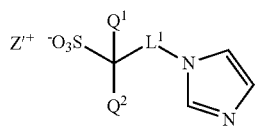

wherein $Q^1$, $Q^2$, $L^1$ and $Z'^+$ are the same as defined above, with a compound represented by the formula (IV):

$$Y-X^1-L^2-H \quad (IV)$$

wherein $L^2$, $X^1$ and Y are the same as defined above;

<11> The process according to <10>, wherein $L^2$ is —O—.

DESCRIPTION OF PREFERRED EMBODIMENTS

The salt of the present invention is a salt represented by the formula (I0):

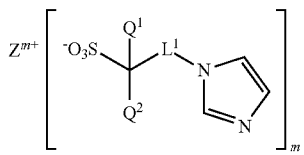

wherein $Q^1$ and $Q^2$ each independently represent a fluorine atom or a C1-C6 perfluoroalkyl group, $L^{10}$ represents a divalent C1-C17 hydrocarbon group in which one or more —CH$_2$— can be replaced by —O— or —CO—, m represents 1 or 2, and $Z^{m+}$ represents m-valent organic or inorganic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the divalent C1-C17 hydrocarbon group include a divalent C1-C17 saturated hydrocarbon group and a divalent C6-C17 nonsaturated hydrocarbon group.

$L^{10}$ is preferably a divalent C1-C17 saturated hydrocarbon group in which one or more —CH$_2$— can be replaced by —O— or —CO—.

Examples of the divalent C1-C17 saturated hydrocarbon group include a linear alkanediyl group, a branched alkanediyl group, a divalent monocyclic or polycyclic saturated hydrocarbon group and a group formed by combining two or more groups selected from the group consisting of the above-mentioned groups.

Examples of the linear alkanediyl group include a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, a methylidene group, an ethylidene group, a propylidene group and an isopropylidene group. Examples of the branched alkanediyl group include a 1-methylpropane-1,3-diyl group, a 2-methylpropane-1,3-diyl group, a 2-methylpropane-1,2-diyl group, a 1-methylbutane-1,4-diyl group and a 2-methylbutane-1,4-diyl group. Examples of the divalent monocyclic saturated hydrocarbon group include a cyclobutane-1,3-diyl group, a cyclopentane-1,3-diyl group, a cyclohexane-1,4-diyl group and a cyclooctane-1,5-diyl group. Examples of the divalent polycyclic saturated hydrocarbon group such as a norbornane-1,4-diyl group, a norbornane-2,5-diyl group, an adamantane-1,5-diyl group and an adamantane-2,6-diyl group.

Examples of the divalent C6-C17 nonsaturated hydrocarbon group include a divalent aromatic hydrocarbon group such as a phenylene group, and a group formed by combining divalent aromatic hydrocarbon group with one or more groups selected from the group consisting of the above-mentioned divalent C1-C17 saturated hydrocarbon groups.

Examples of the C1-C17 hydrocarbon group in which one or more —CH$_2$— are replaced by —O— or —CO— include *—CO—, *—CO—O—L$^{b1}$-CO—, *-L$^{b2}$-O—CO— and *—CO—O-L$^{b3}$-O—CO—, wherein L$^{b1}$ represents a C1-C14 alkanediyl group, L$^{b2}$ represents a C1-C15 alkanediyl group or a phenylene group, L$^{b3}$ represents a C1-C13 saturated hydrocarbon group, and * represents a binding position to —C(Q$^1$)(Q$^2$)-. Among them, preferred are *—CO—, *—CO—O-L$^{b1}$-CO— and *-L$^{b2}$-O—CO—, and more preferred are *—CO— and *—CO—O-L$^{b1}$-CO—, and much more preferred is *—CO—.

Examples of *—CO—O-L$^{b1}$- include the following.

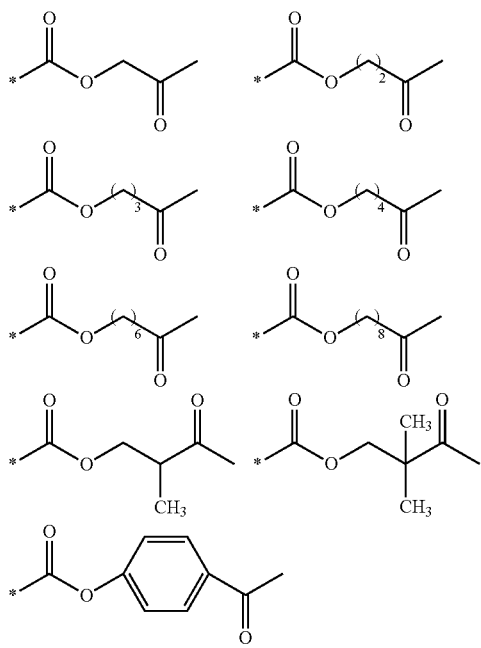

Examples of *-L$^{b2}$-O—CO— include the following.

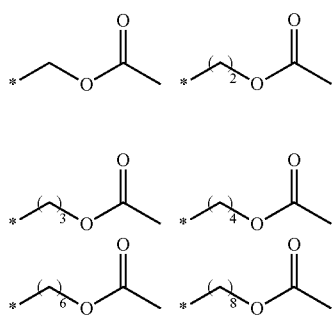

Examples of *—CO—O-L$^{b3}$-O—CO— include the following.

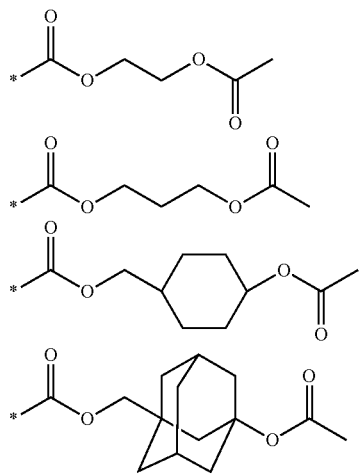

In the formula (I0), m is 1 or 2, and m is preferably 1.

Preferable examples of the salt represented by the formula (I0) include a salt represented by the formula (I):

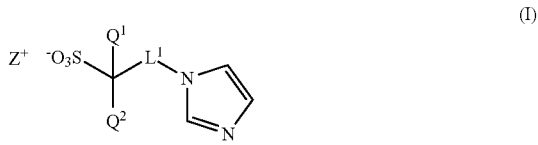

(I)

wherein Q$^1$ and Q$^2$ are the same as defined above, L$^1$ represents a divalent C1-C17 saturated hydrocarbon group in which one or more —CH$_2$— can be replaced by —O— or —CO—, and Z$^+$ represents monovalent organic or inorganic cation.

Examples of the salt represented by the formula (I0) include the following.

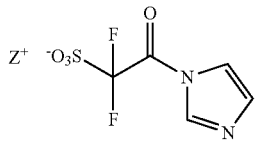

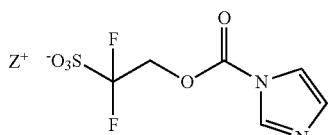

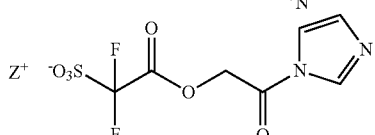

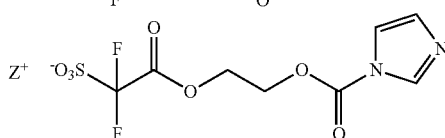

$Z^{m+}$ represents a m-valent organic or inorganic cation, and examples of the organic cation include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable. Examples of the inorganic cation include an alkali metal cation such as a sodium cation and a potassium cation, and a sodium cation is preferable.

Preferable examples of the organic cation include the cations represented by the formulae (b2-1) to (b2-4):

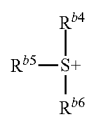
(b2-1)

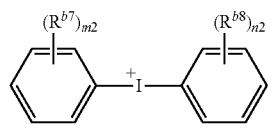
(b2-2)

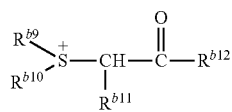
(b2-3)

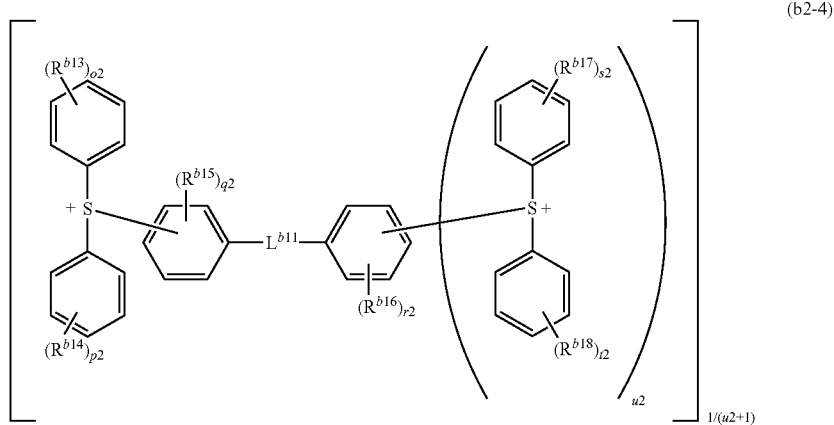
(b2-4)

wherein $R^{b4}$, $R^{b5}$ and $R^{b6}$ independently represent a C1-C30 alkyl group which can have one or more substituents selected from the group consisting of a hydroxyl group, a C1-C12 alkoxy group and a C6-C18 aromatic hydrocarbon group, a C3-C36 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C36 alkyl group, a C3-C36 saturated cyclic hydrocarbon group and a C1-C12 alkoxy group, $R^{b7}$ and $R^{b8}$ are independently in each occurrence a hydroxyl group, a C1-C12 alkyl group or a C1-C12 alkoxy group, m2 and n2 independently represents an integer of 0 to 5, $R^{b9}$ and $R^{b10}$ independently represent a C1-C36 alkyl group or a C3-C36 saturated cyclic hydrocarbon group, or $R^{b9}$ and $R^{b10}$ are bonded to form a C2-C11 divalent acyclic hydrocarbon group which forms a ring together with the adjacent $S^+$, and one or more —CH$_2$— in the divalent acyclic hydrocarbon group may be replaced by —CO—, —O— or —S—, and
$R^{b11}$ represents a hydrogen atom, a C1-C36 alkyl group, a C3-C36 saturated cyclic hydrocarbon group or a C6-C18 aromatic hydrocarbon group, $R^{b12}$ represents a C1-C12 alkyl group, a C3-C18 saturated cyclic hydrocarbon group or a C6-C18 aromatic hydrocarbon group and the aromatic hydrocarbon group can have one or more substituents selected from the group consisting of a C1-C12 alkyl group, a C1-C12 alkoxy group, a C3-C18 saturated cyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —CH$_2$— in the divalent acyclic hydrocarbon group may be replaced by —CO—, —O— or —S—, and
$R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The alkyl group represented by $R^{b9}$ to $R^{b11}$ has preferably 1 to 12 carbon atoms. The saturated cyclic hydrocarbon group represented by $R^{b9}$ to $R^{b11}$ has preferably 3 to 36 carbon atoms and more preferably 4 to 12 carbon atoms.

Preferable examples of the alkyl group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the cyclic aliphatic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the alkyl group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

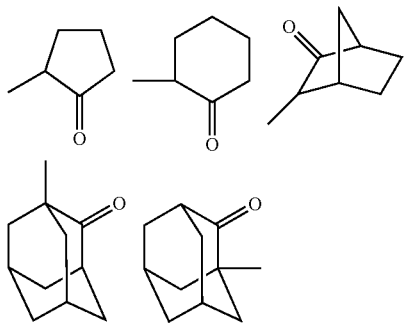

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation is especially preferable.

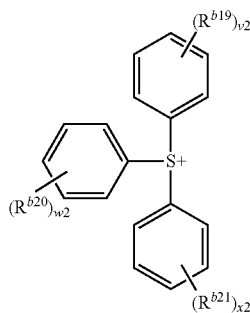

(b2-1-1)

wherein $R^{b19}$, $R^{b20}$ and $R^{b21}$ are independently in each occurrence a halogen atom (preferably a fluorine atom), a hydroxyl group, a C1-C36 alkyl group, a C3-C36 saturated cyclic hydrocarbon group or a C1-C12 alkoxy group, and one or more hydrogen atoms of the alkyl group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and v2, w2 and x2 independently each represent an integer of 0 to 5.

The alkyl group has preferably 1 to 12 carbon atoms, and the saturated cyclic hydrocarbon group has preferably 4 to 36 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

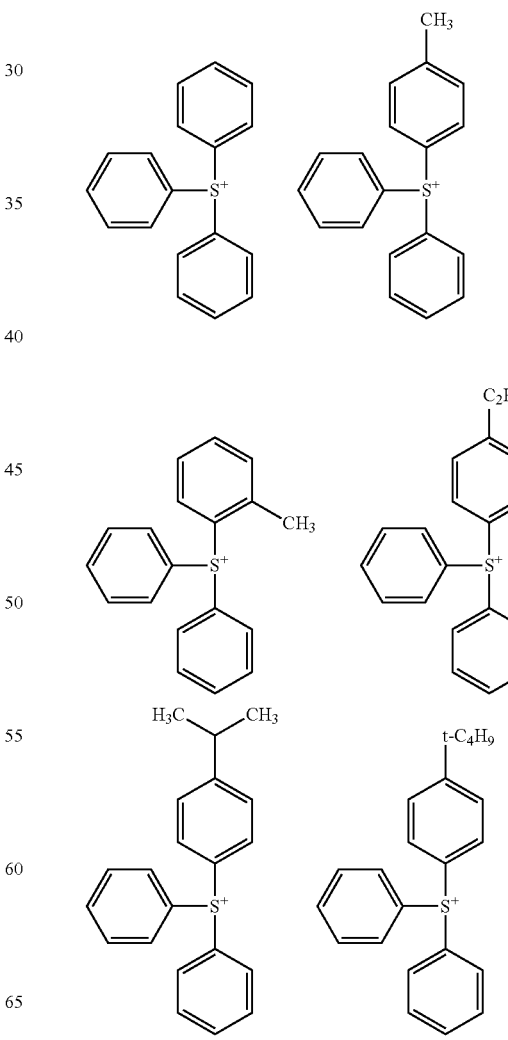

-continued
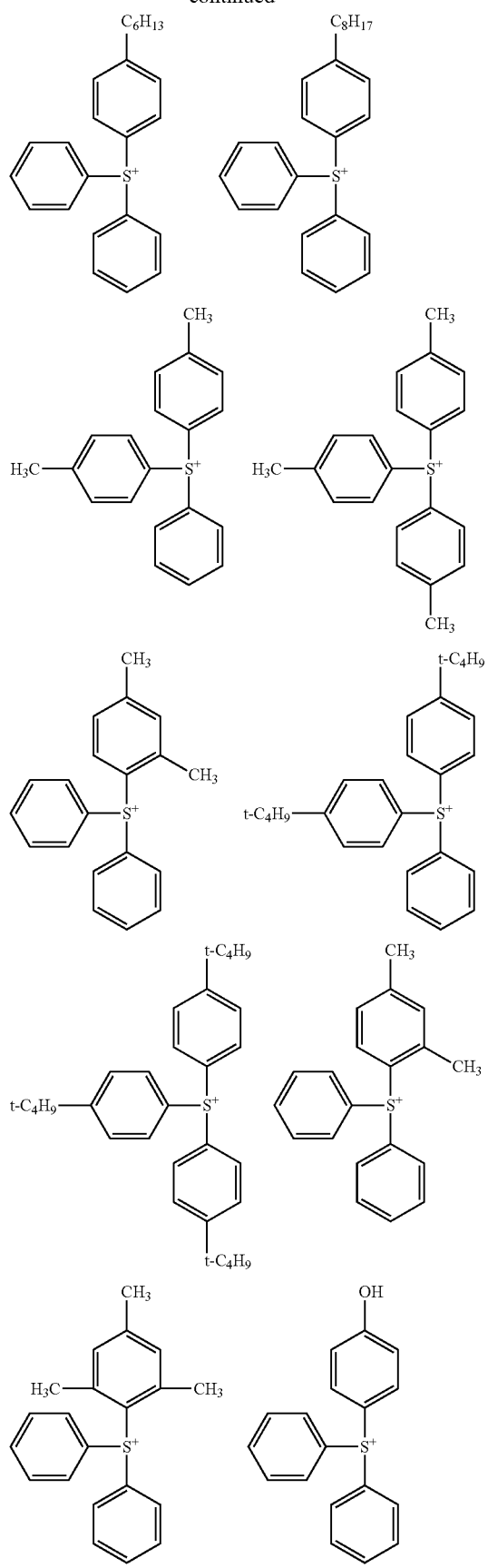
-continued
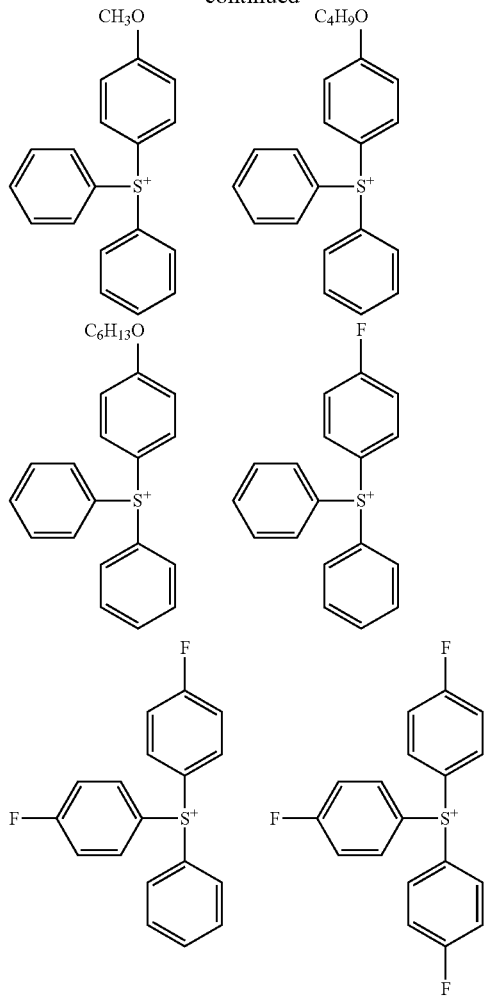
Examples of the cation represented by the formula (b2-2) include the followings.
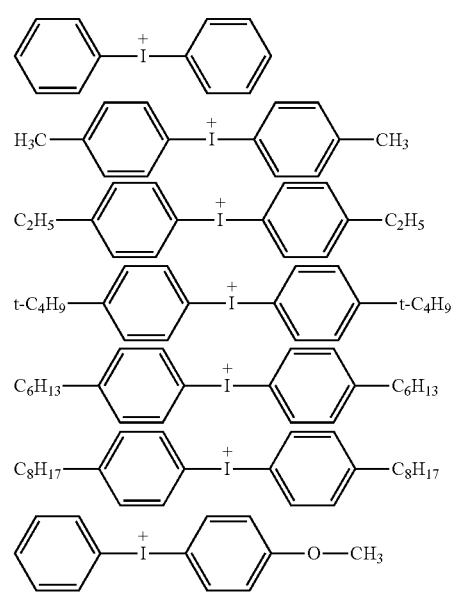

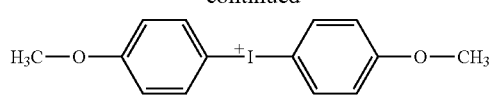
Examples of the cation represented by the formula (b2-3) include the followings.
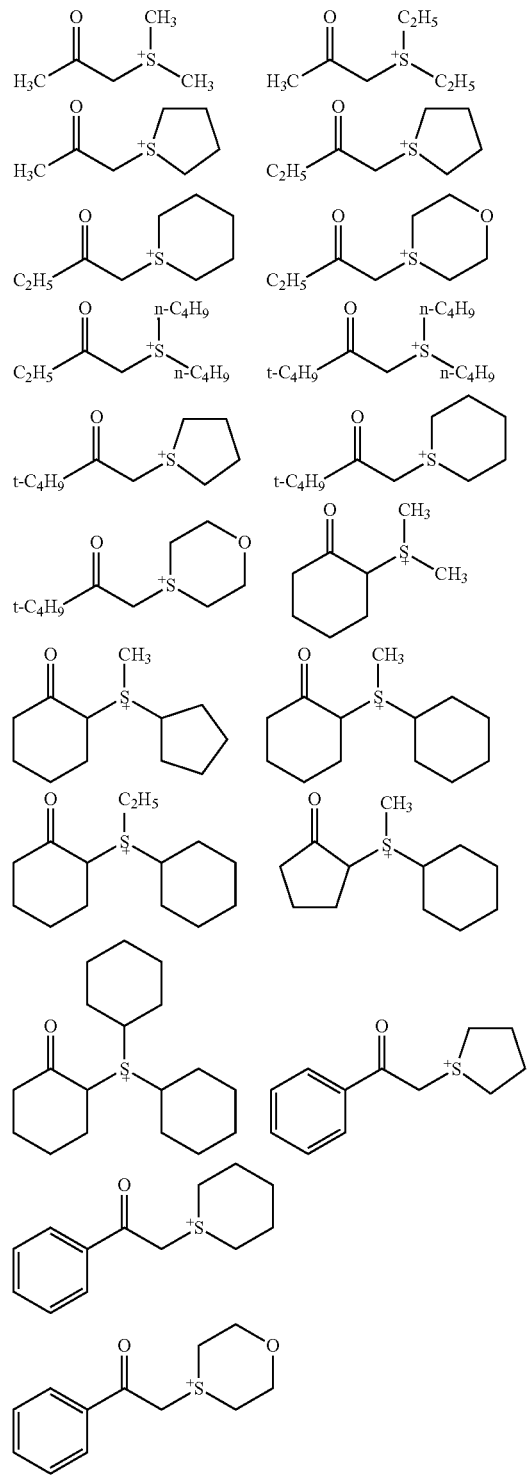
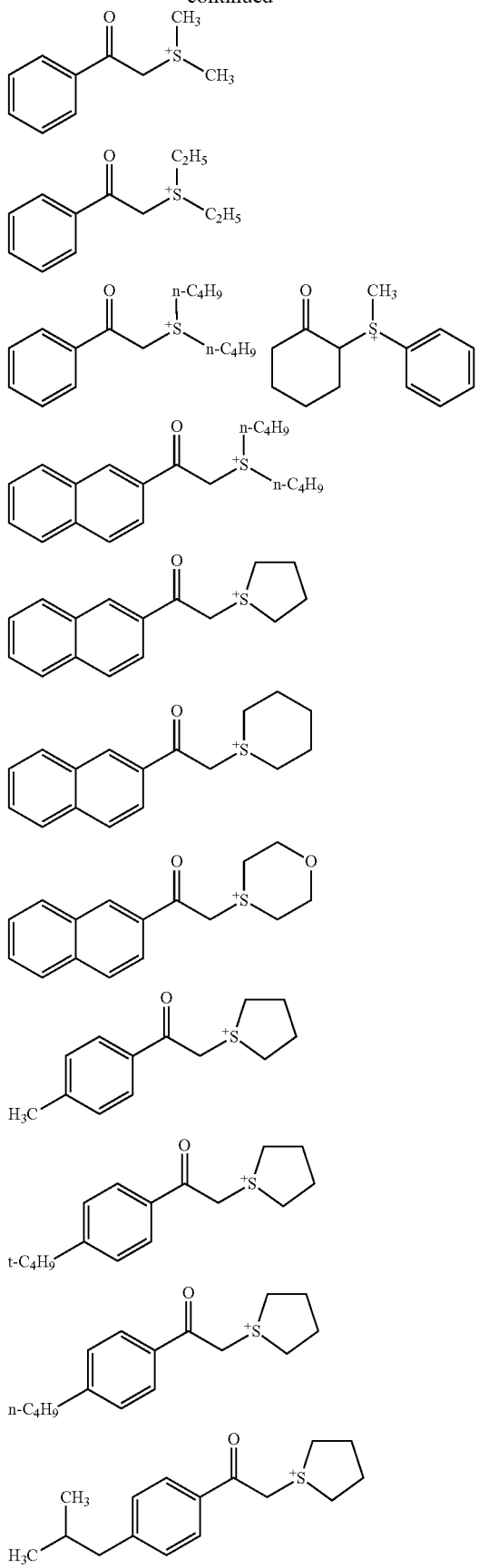

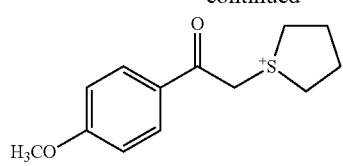
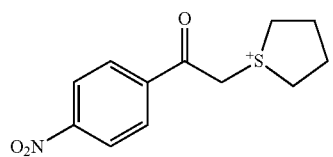
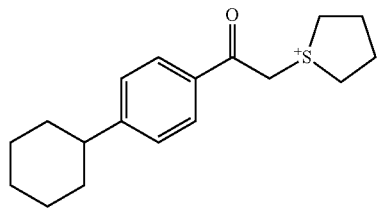
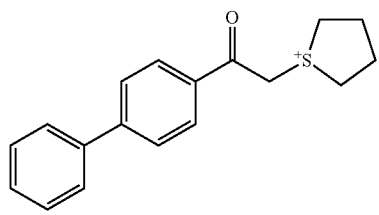
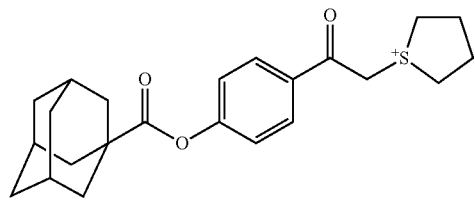
Examples of the cation represented by the formula (b2-4) include the followings.
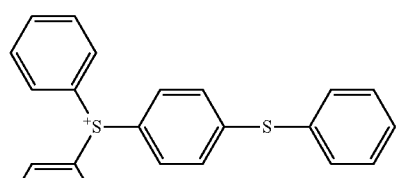
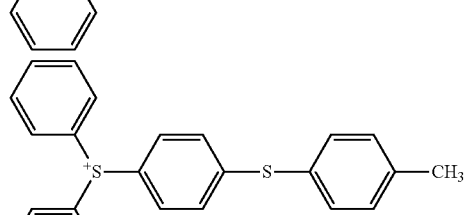
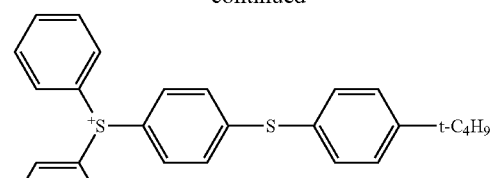
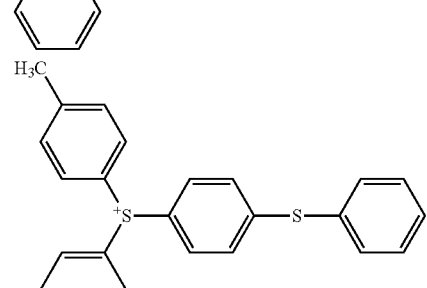
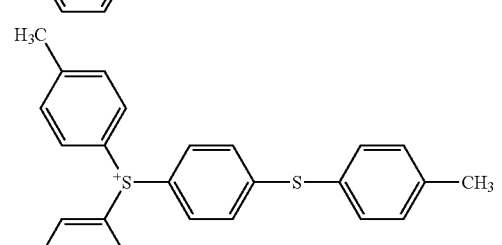
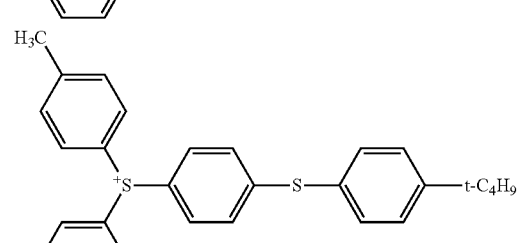
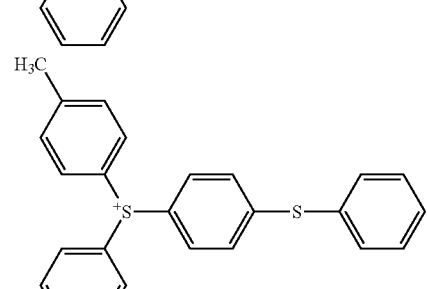
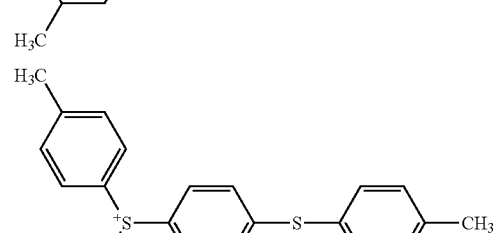

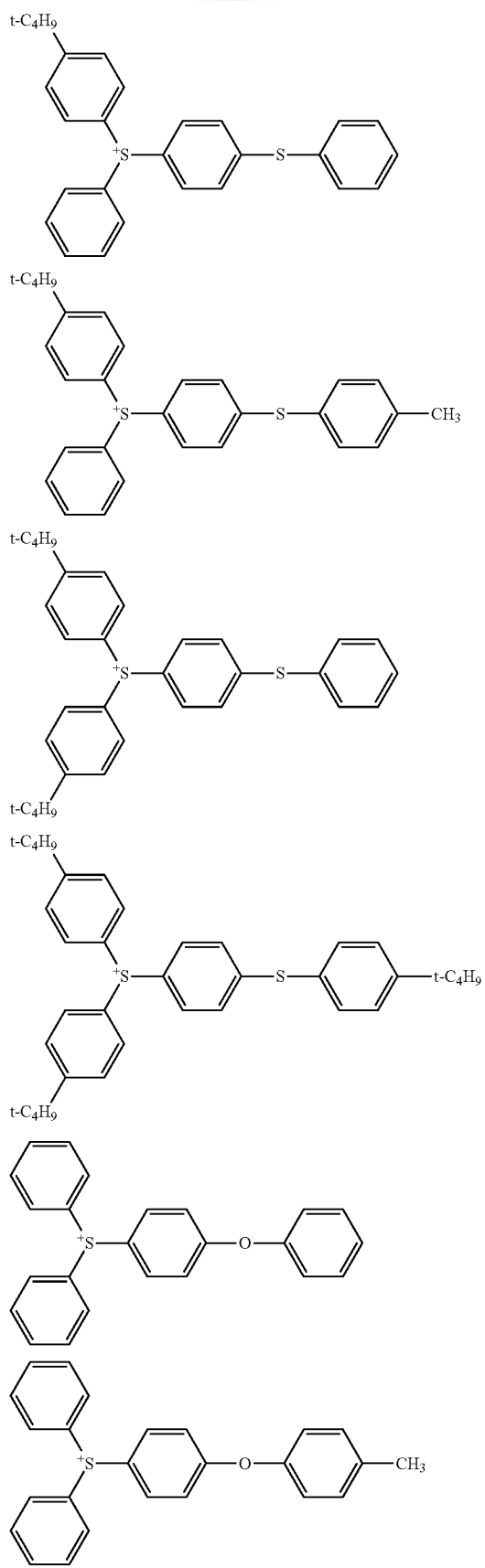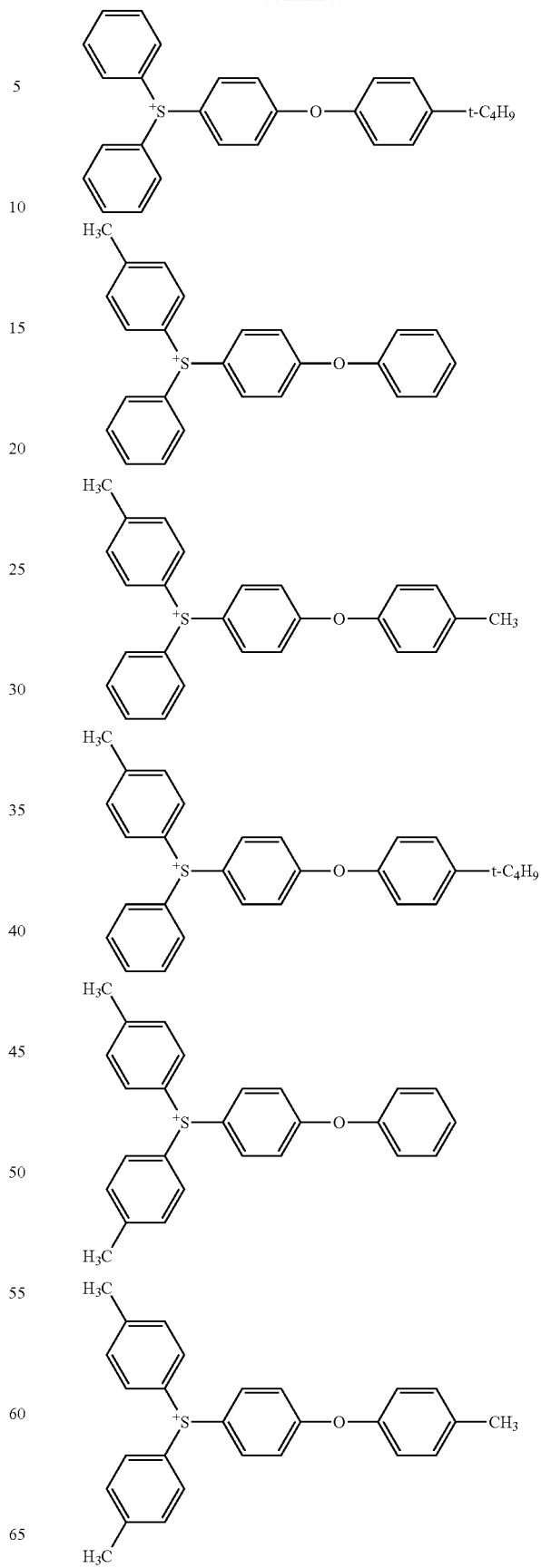

-continued
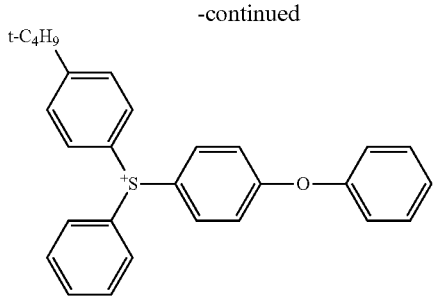
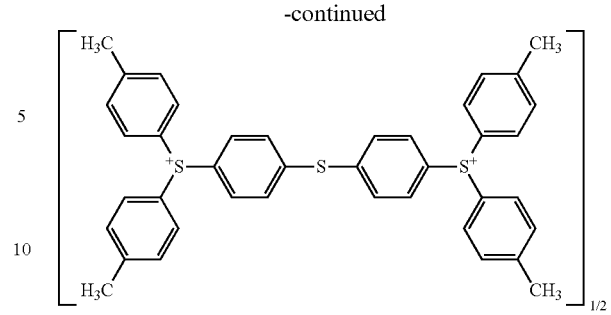
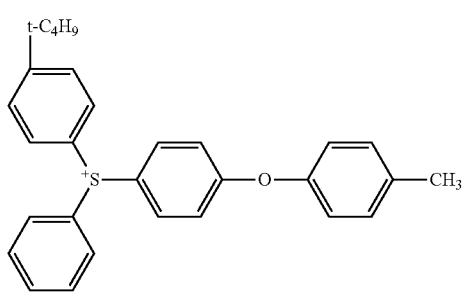
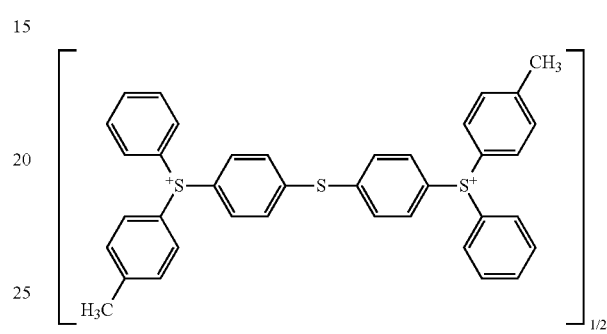
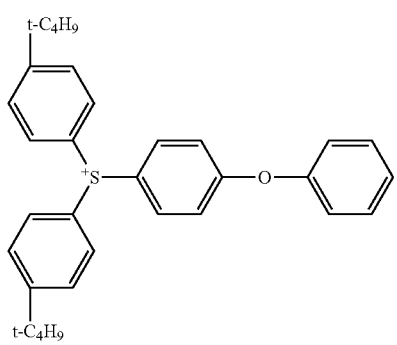
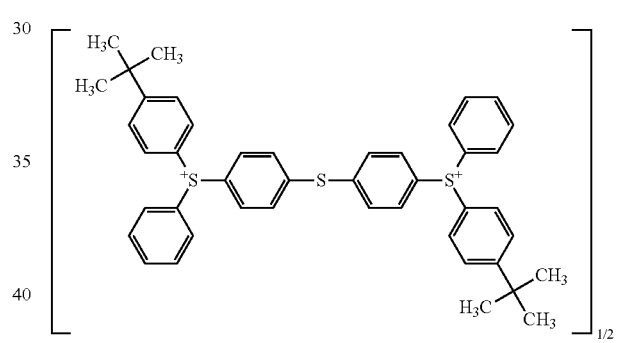
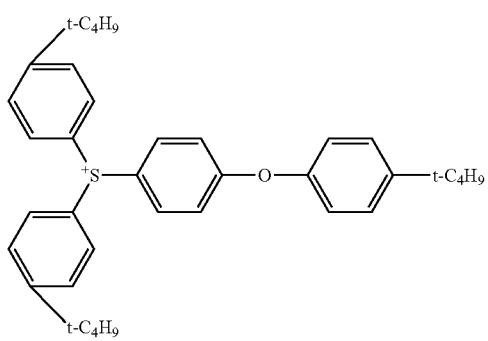
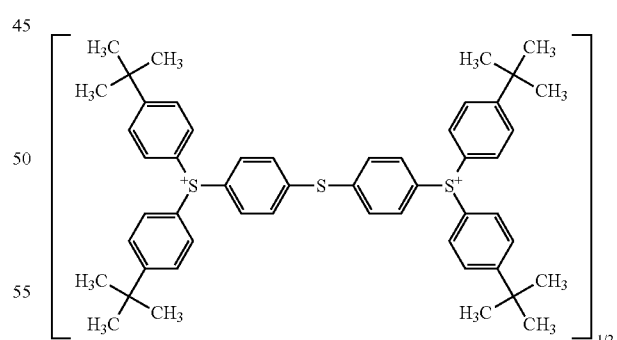
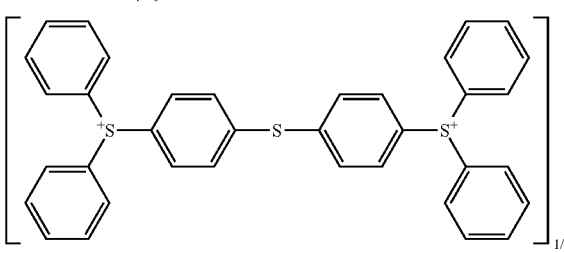
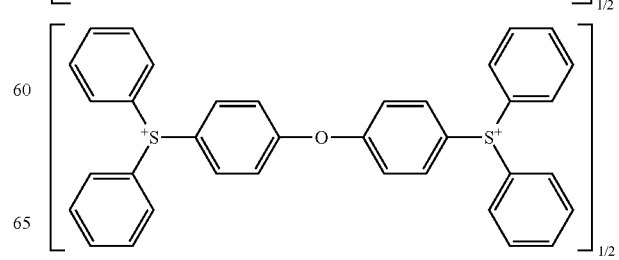

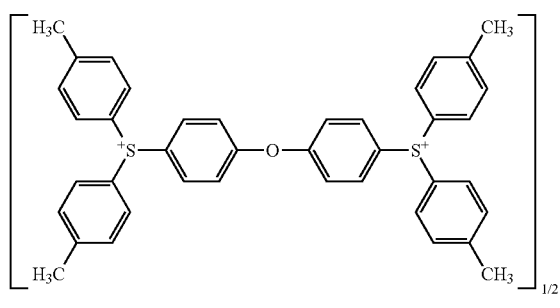
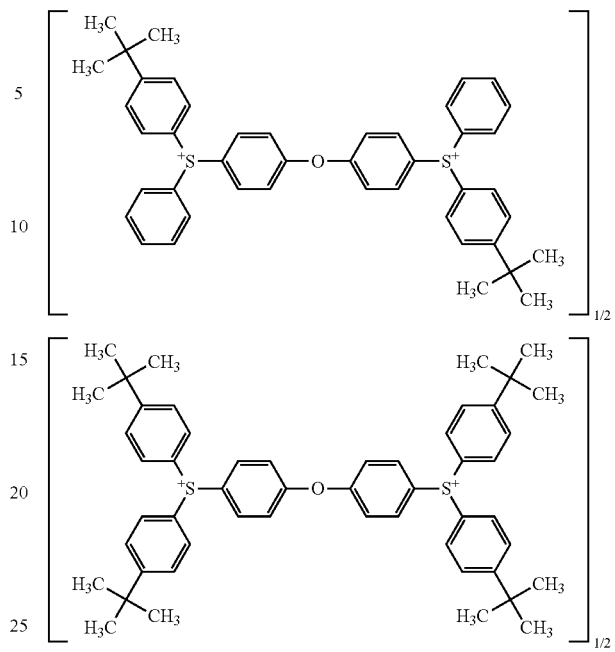
Examples of the salt represented by the formula (I0) include a salt wherein the anion part is any one of the above-mentioned anion parts and the cation part is any one of organic or inorganic cation parts. Preferable examples of the salt represented by the formula (I0) include the salts represented by the formulae (I-1) to (I-48).
(I-1)
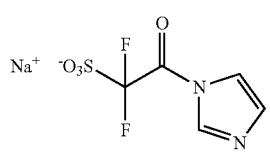
(I-2)
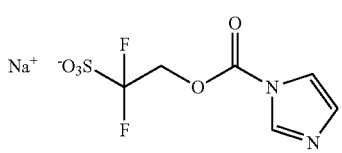
(I-3)
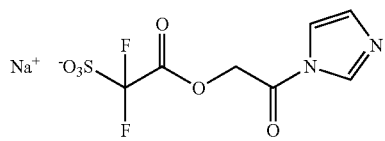
(I-4)
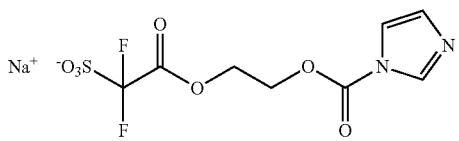
(I-5)
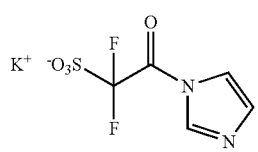
(I-6)
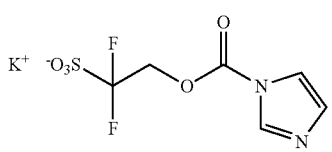
(I-7)
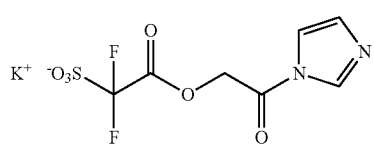
(I-8)
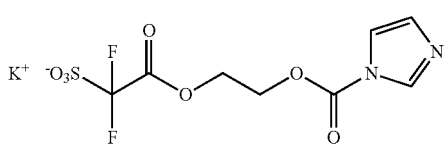

-continued
(I-9)
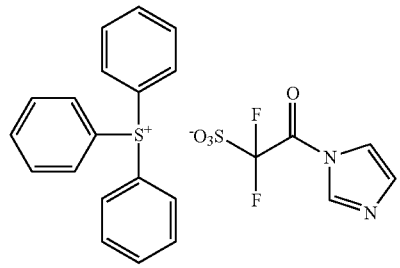
(I-10)
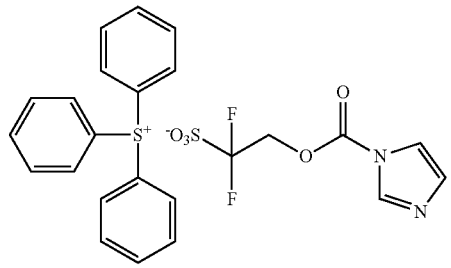
(I-11)
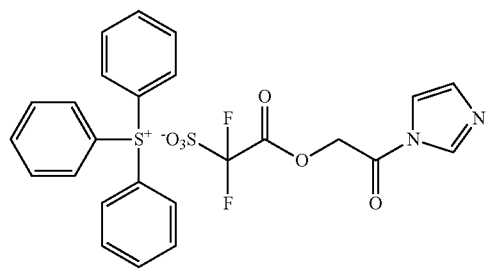
(I-12)
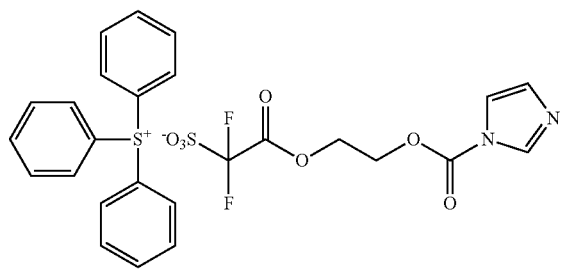
(I-13)
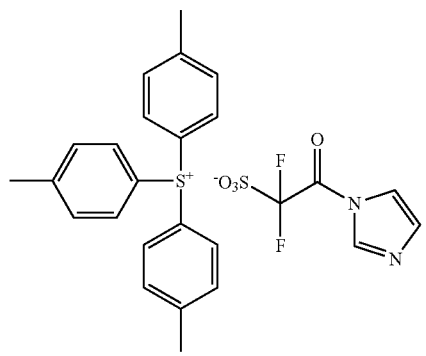
(I-14)
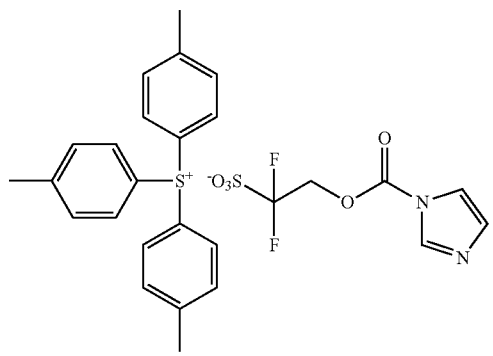
(I-15)
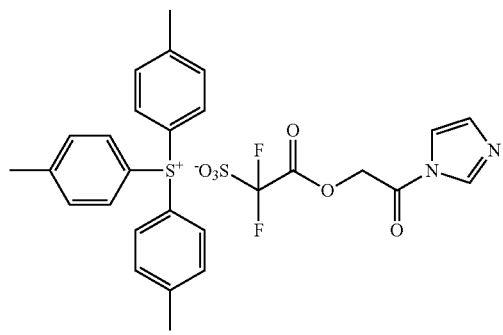
(I-16)
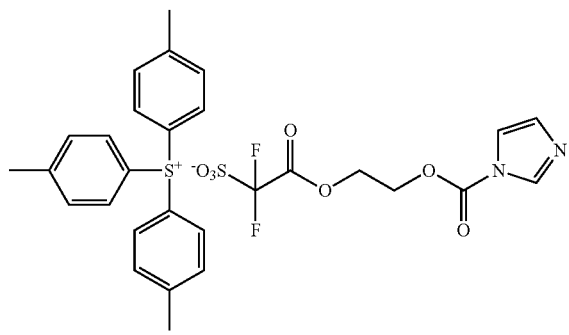
(I-17)
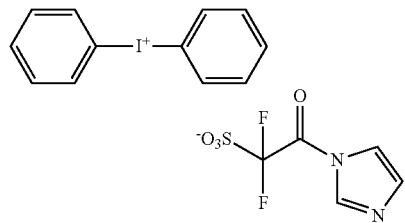
(I-18)
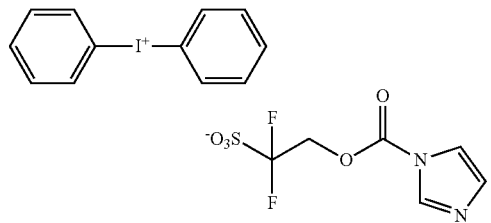

-continued
(I-19)
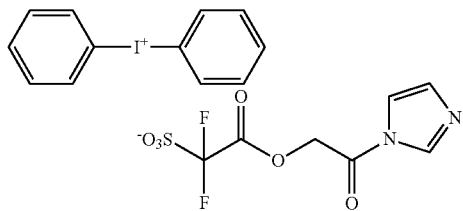
(I-20)
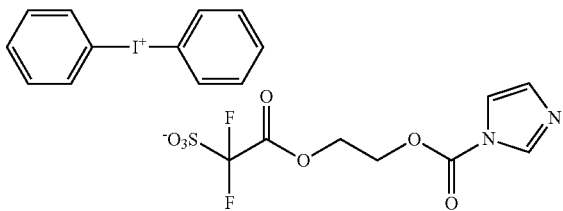
(I-21)
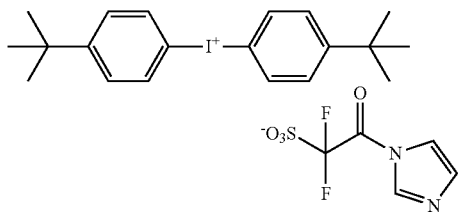
(I-22)
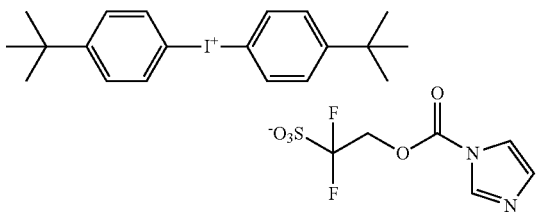
(I-23)
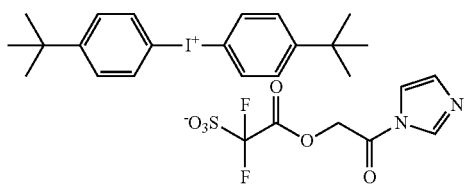
(I-24)
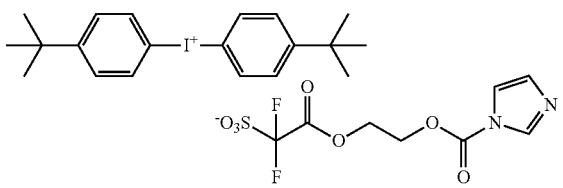
(I-25)
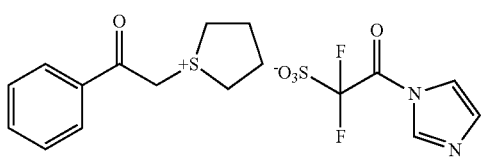
(I-26)
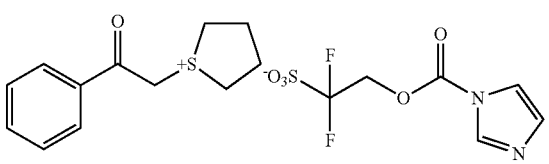
(I-27)
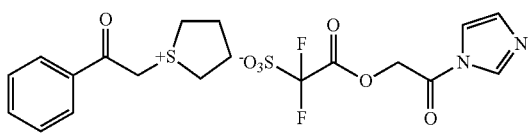
(I-28)
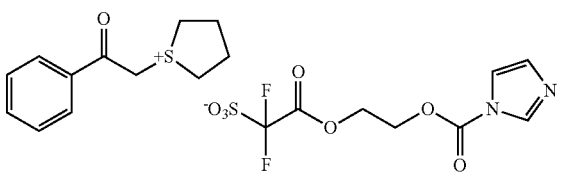
(I-29)
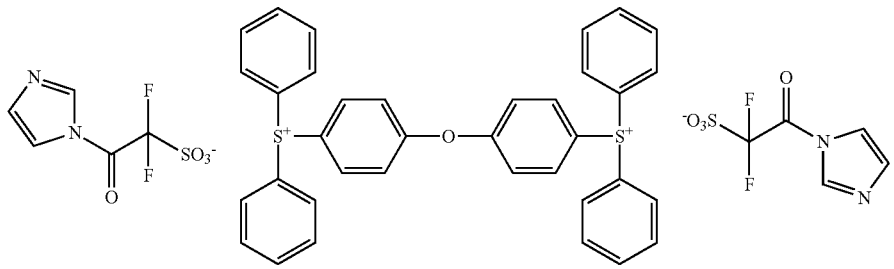
(I-30)
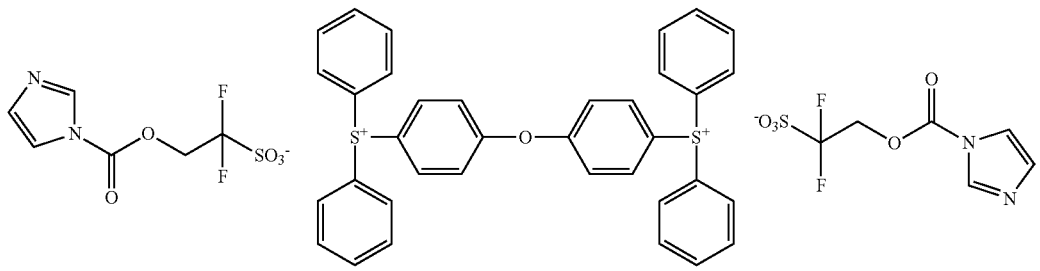

-continued
(I-31)
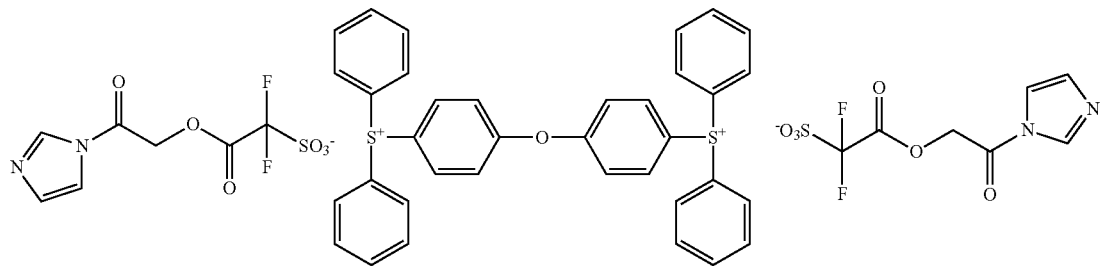
(I-32)
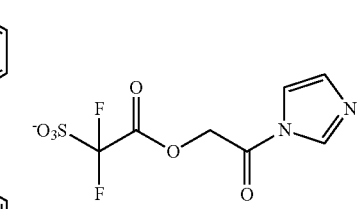
(I-33)
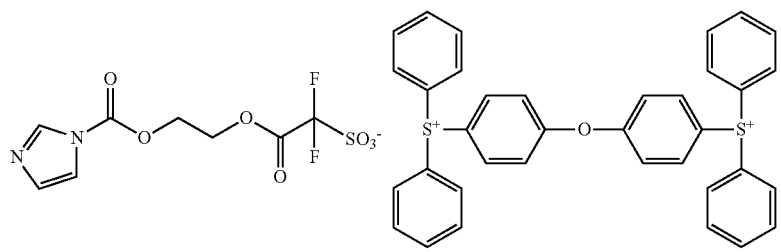
(I-34)
(I-35)
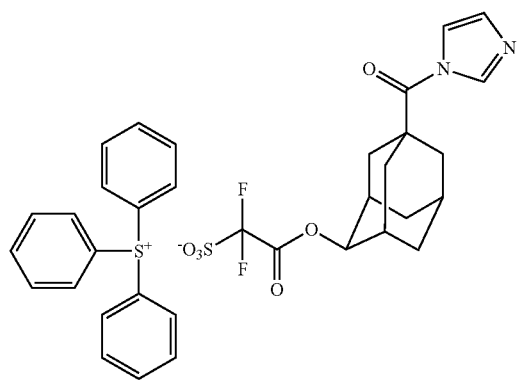
(I-36)
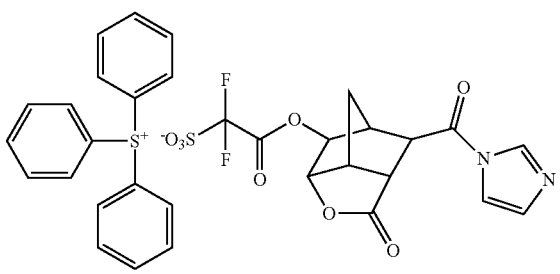
(I-37)
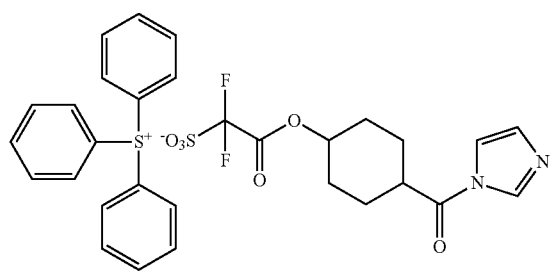
(I-38)
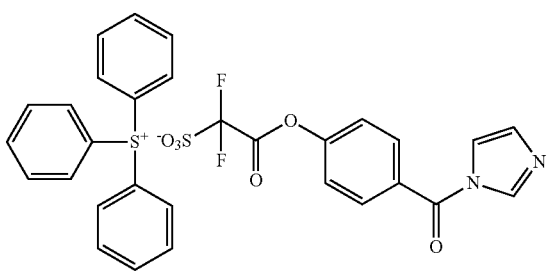
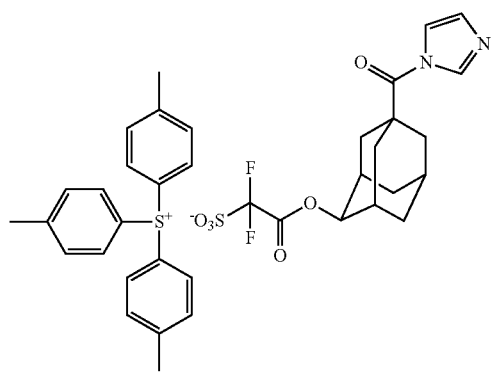
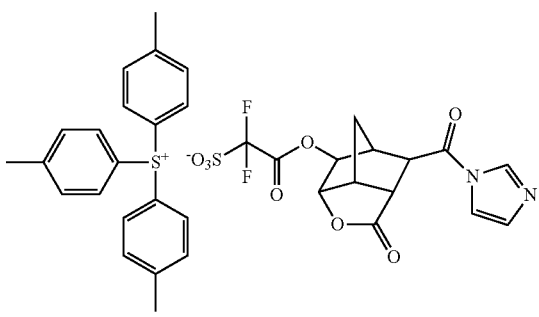

(I-39)
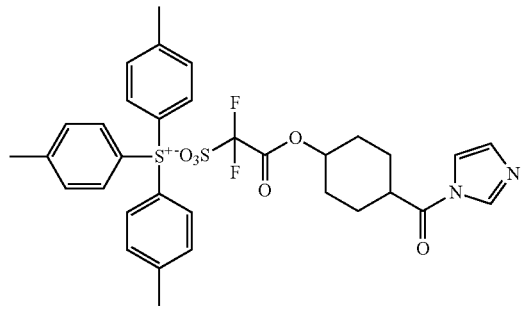
(I-40)
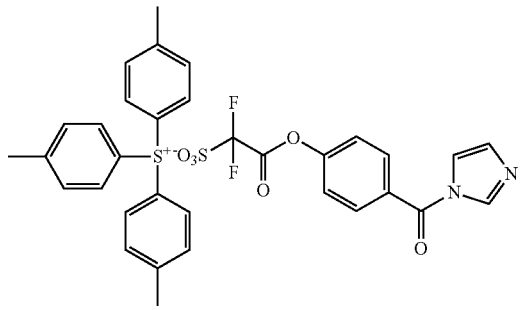
(I-41)
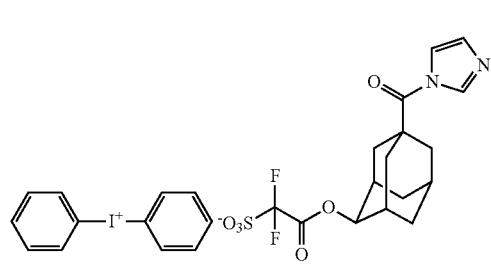
(I-42)
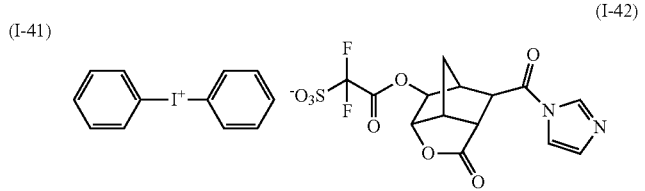
(I-43)
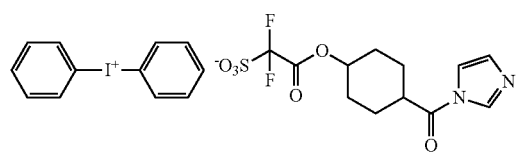
(I-44)
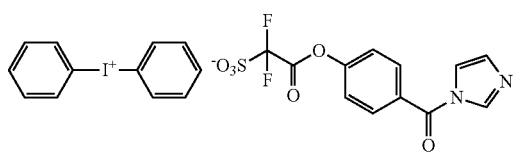
(I-45)
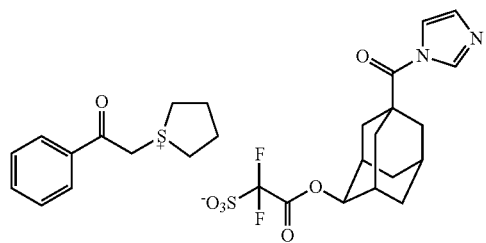
(I-46)
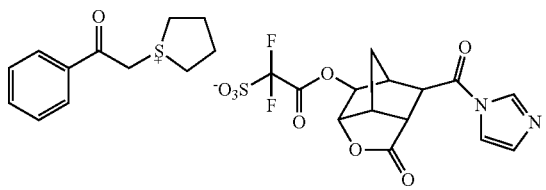
(I-47)
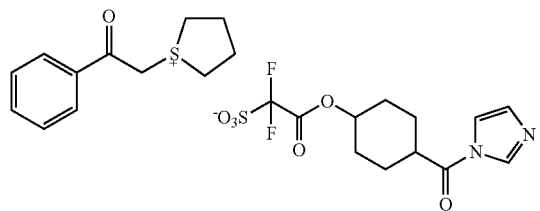
(I-48)
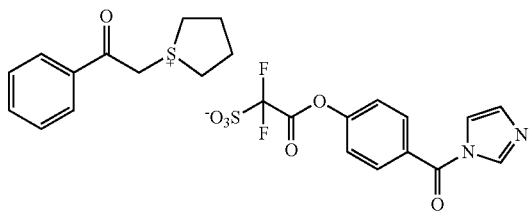

Among them, preferred are the salts represented by the formulae (I-1), (I-2), (I-9), (I-10), (I-13), (I-14), (I-17), (I-18), (I-21), (I-22), (I-25), (I-26), (I-33), (I-34), (I-37) and (I-38), and more preferred are the salts represented by the formulae (I-1), (I-9), (I-13), (I-17), (I-33) and (I-37), and especially preferred are the salts represented by the formulae (I-1), (I-9), (I-13) and (I-33).

The salt represented by the formula (I) can be produced by a process comprising reacting a salt represented by the formula (II):

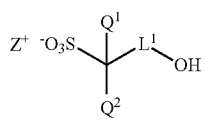

(II)

wherein $Q^1$, $Q^2$, $L^1$ and $Z^+$ are the same as defined above, with carbonyldiimidazole in a solvent such as acetonitrile at 5 to 90° C., preferably at 20 to 60° C. The salt represented by the formula (II) can be produced, for example, according to the method described in JP 2008-127367 A.

The amount of carbonyldiimidazole is usually 1.0 to 3.0 moles per 1 mole of the salt represented by the formula (II), and preferably 1.0 to 2.0 moles. The amount of the solvent is usually 1.5 to 10 parts by weight per 1 part by weight of sum of carbonyldiimidazole and the salt represented by the formula (II), and preferably 2 to 5 parts by weight.

An acid generator can be produced in a high yield from the salt represented by the formula (I).

Examples of the acid generator include a salt represented by the formula (B1):

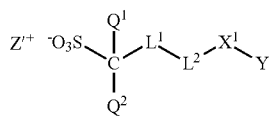

(B1)

wherein $Q^1$, $Q^2$ and $L^1$ are the same as defined above, $L^2$ represents —O— or —HR$^3$— in which $R^3$ represents a hydrogen atom or a C1-C4 alkyl group, $X^1$ represents a single bond or a C1-C6 alkanediyl group, Y represents a C1-C18 alkyl group which can have one or more substituents or a C3-C18 saturated cyclic hydrocarbon group which can have one or more substituents and one or more —CH$_2$— in the alkyl group and the saturated cyclic hydrocarbon group can be replaced by —O—, —SO$_2$— or —CO—, and $Z'^+$ represents a monovalent organic cation.

The salt represented by the formula (B1) can be produced by reacting a salt represented by the formula (I'):

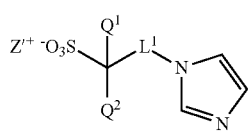

(I')

wherein $Q^1$, $Q^2$, $L^1$ and $Z'^+$ are the same as defined above, with a compound represented by the formula (IV):

Y—X$^1$-L$^2$-H          (IV)

wherein $L^2$, $X^1$ and Y are the same as defined above.

The reaction of the salt represented by the formula (I') with the compound represented by the formula (IV) is usually conducted in a solvent and examples of the solvent include acetonitrile and chloroform. The reaction temperature is usually 5 to 90° C. and preferably 20 to 60° C.

The amount of the compound represented by the formula (IV) is usually 1.0 to 1.5 moles per 1 mole of the salt represented by the formula (I') and preferably 1.0 to 1.2 moles.

The amount of the solvent is usually 1.5 to 10 parts by weight per 1 part by weight of sum of the salt represented by the formula (I') and the compound represented by the formula (IV) and preferably 2 to 5 parts by weight.

The salt represented by the formula (B1) can also be produced by reacting a salt represented by the formula (I"):

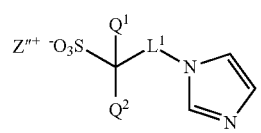

(I")

wherein $Q^1$, $Q^2$ and $L^1$ are the same as defined above and $Z''^+$ represents an inorganic cation, with a compound represented by the formula (IV):

Y—X$^1$-L$^2$-H          (IV)

wherein $L^2$, $X^1$ and Y are the same as defined above, to obtain a salt represented by the formula (V):

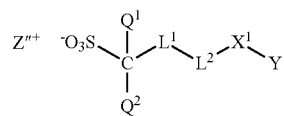

(V)

wherein $Q^1$, $Q^2$, $L^1$, $L^2X^1$, Y and $Z''^+$ are the same as defined above, followed by reacting the salt represented by the formula (V) with a salt represented by the formula (VI):

Z'$^+$X'$^-$          (VI)

wherein $Z'^+$ is the same as defined above and $X'^-$ represents a halogen anion.

The reaction of the salt represented by the formula (I") with the compound represented by the formula (IV) and the reaction of the salt represented by the formula (V) with the salt represented by the formula (VI) are usually conducted in a solvent, respectively, and examples of the solvent include acetonitrile and chloroform.

The reaction temperatures of the above-mentioned reactions are usually 5 to 90° C. and preferably 20 to 60° C.

The amount of the compound represented by the formula (IV) is usually 1.0 to 1.5 moles per 1 mole of the salt represented by the formula (I") and preferably 1.0 to 1.2 moles.

The amount of the solvent is usually 1.5 to 10 parts by weight per 1 part by weight of sum of the salt represented by the formula (I") and the compound represented by the formula (IV) and preferably 2 to 5 parts by weight.

Examples of the C1-C6 alkanediyl group represented by $X^1$ include a methylene group, an ethylene group, a propane- 1,3-diyl group, a propane-1,2-diyl group, a butane-1,4-diyl group, a pentane-1,5-diyl group and a hexane-1,6-diyl group, and $X^1$ is preferably a single bond or a methylene group.

Examples of the C1-C4 alkyl group represented by $R^3$ include a methyl group, an ethyl group, a propyl group, an isopropyl group, a butyl group and a tert-butyl group. Examples of $L^2$ include —O—, —NH—, —N(CH$_3$)—, —N(C$_2$H$_5$)—, —N(C$_3$H$_7$)— and —N(C$_4$H$_9$)—, and $L^2$ is preferably —O— or —NH— and more preferably —O—.

Examples of the substituent in Y include a halogen atom, a hydroxyl group, an oxo group (=O), a glycidyloxy group, a C2-C4 acyl group, a C1-C12 alkoxy group, a C1-C12 alkyl group, a C1-C12 hydroxy-containing alkyl group, a C3-C16 saturated cyclic hydrocarbon group, a C6-C18 aromatic hydrocarbon group, a C7-C21 aralkyl group and —(CH$_2$)$_{j2}$—O—CO—R$^{b1}$— in which R$^{b1}$ represents a C1-C16 alkyl group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkyl group include the same as described above. Examples of the hydroxyl-containing alkyl group include a hydroxymethyl group and a hydroxyethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 alkyl group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C18 saturated cyclic hydrocarbon group represented by Y include the groups represented by the formulae (Y1) to (Y26):

(Y1)

(Y2)

(Y3)

(Y4)

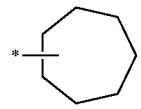
(Y5)

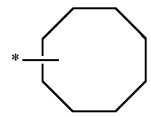
(Y6)

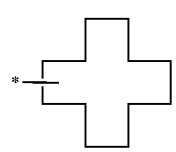
(Y7)

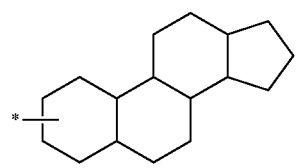
(Y8)

(Y9)

(Y10)

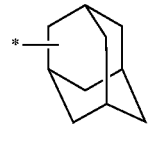
(Y11)

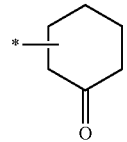
(Y12)

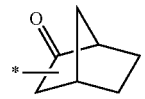
(Y13)

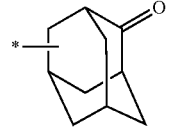
(Y14)

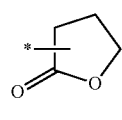
(Y15)

(Y16)

-continued (Y17) 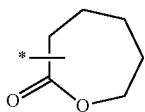

(Y18) 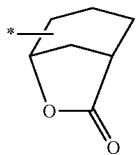

(Y19) 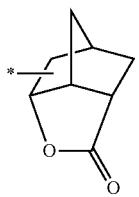

(Y20) 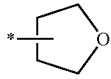

(Y21) 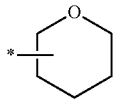

(Y22) 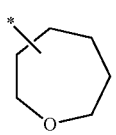

(Y23) 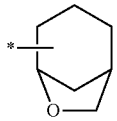

(Y24) 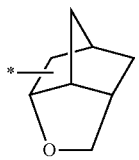

(Y25) 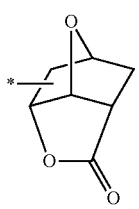

-continued (Y26) 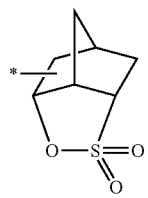

Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.

Examples of Y having one or more substituents include the followings:

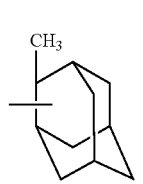 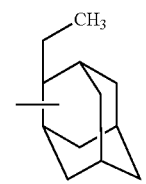 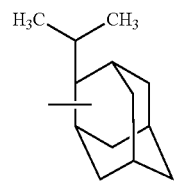

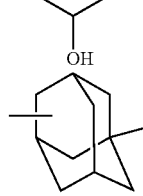 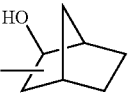 

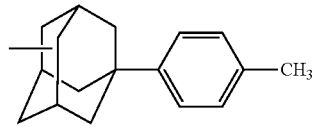

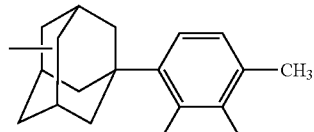

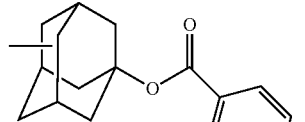

Y is preferably an adamantyl group which can have one or more substituents, and is more preferably an adamantyl group or an oxoadamantyl group.

Preferable examples of the acid generator represented by the formula (B1) include acid generators represented by the formulae (B1-1) to (B1-29), and more preferred are acid generators represented by the formulae (B1-1), (B1-2), (B1-3), (B1-6), (B1-11), (B1-12), (B1-13), (B1-14), (B1-22), (B1-23), (B1-24) and (B1-25), and especially preferred are acid generators represented by the formulae (B1-2), (B1-3), (B1-6), (B1-11), (B1-13), (B1-22) and (B1-24).

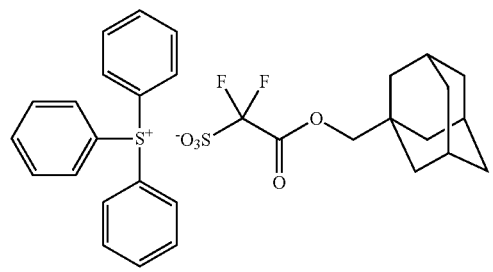
(B1-1)
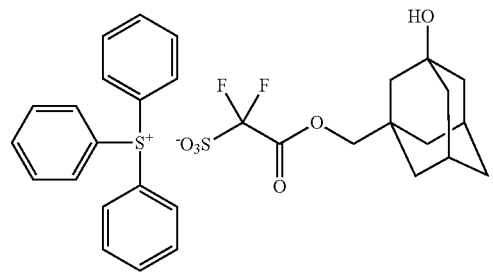
(B1-2)
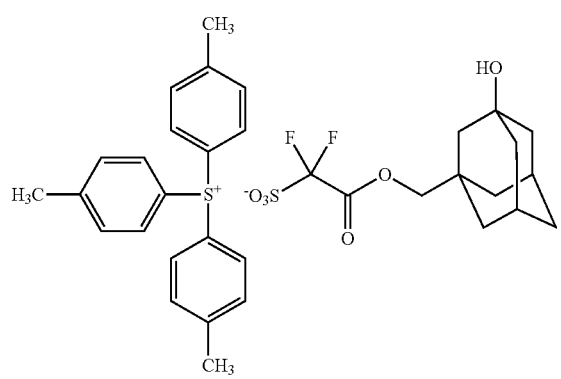
(B1-3)
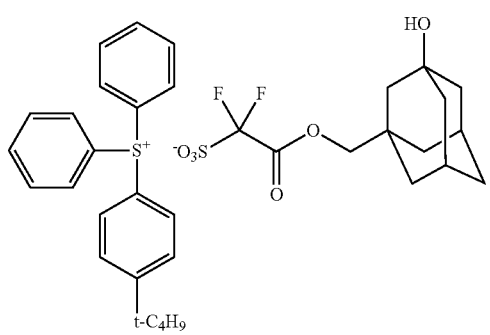
(B1-4)
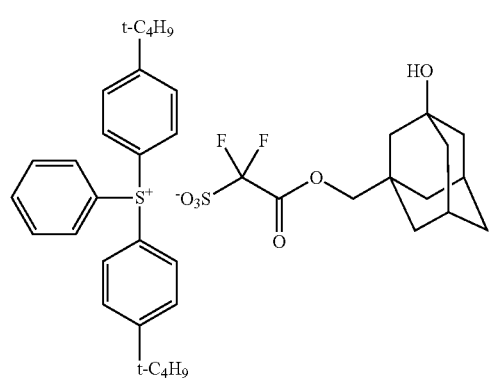
(B1-5)
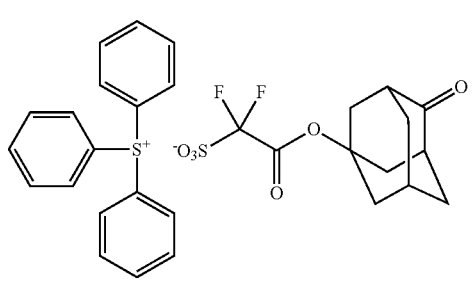
(B1-6)
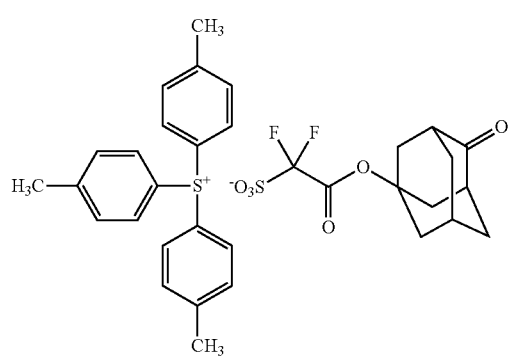
(B1-7)
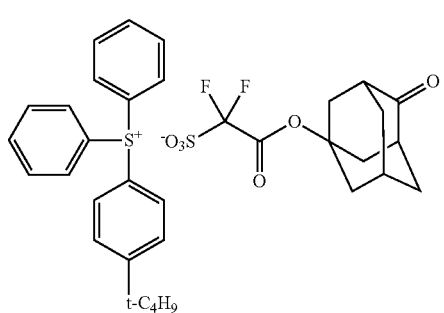
(B1-8)

-continued
(B1-9)
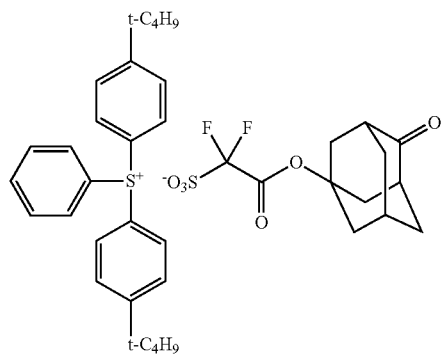
(B1-10)
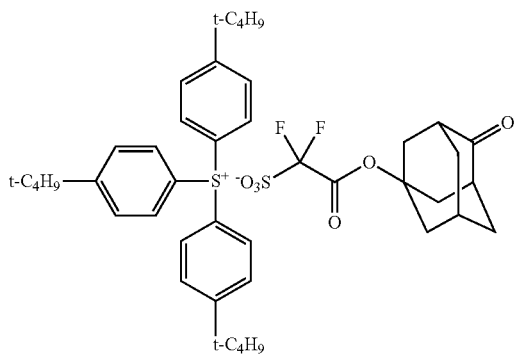
(B1-11)
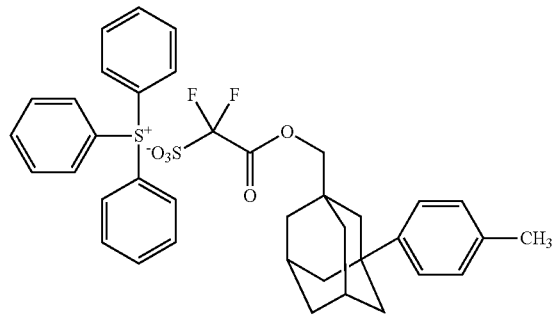
(B1-12)
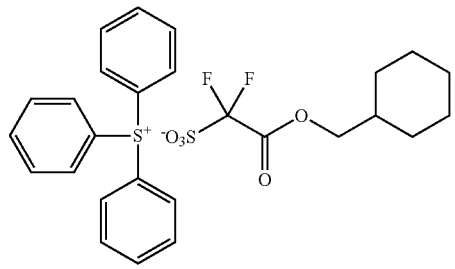
(B1-13)
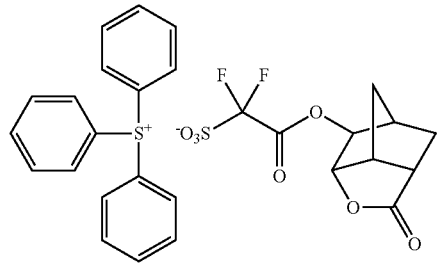
(B1-14)
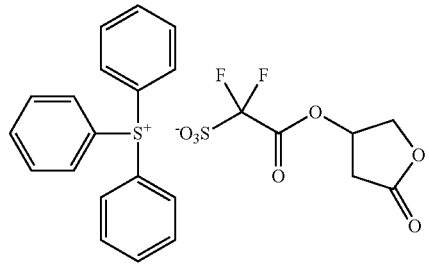
(B1-15)
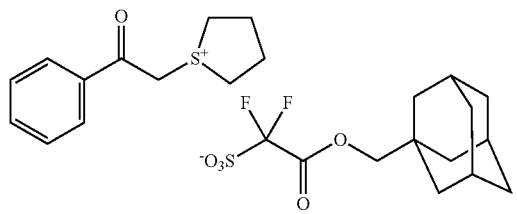
(B1-16)
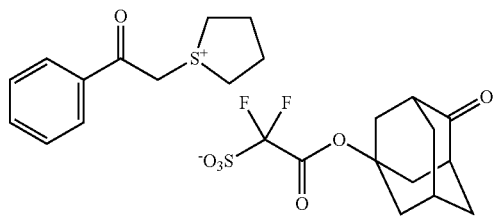
(B1-17)
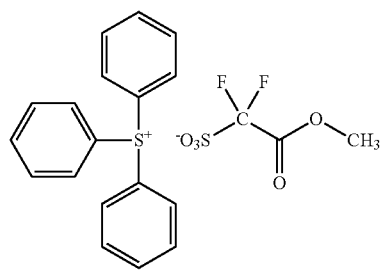
(B1-18)
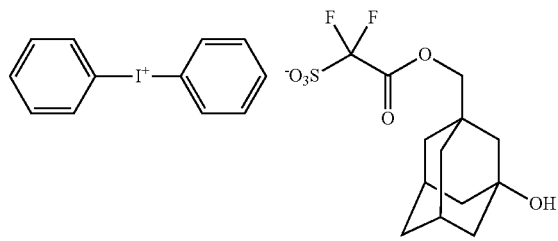

-continued
(B-19)
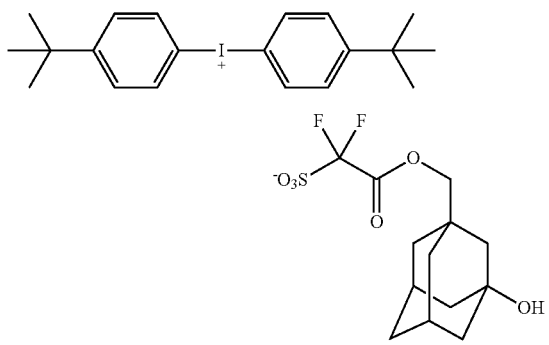
(B1-20)
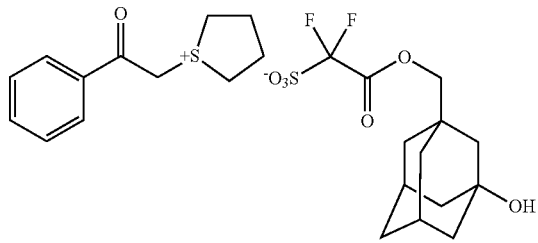
(B1-21)
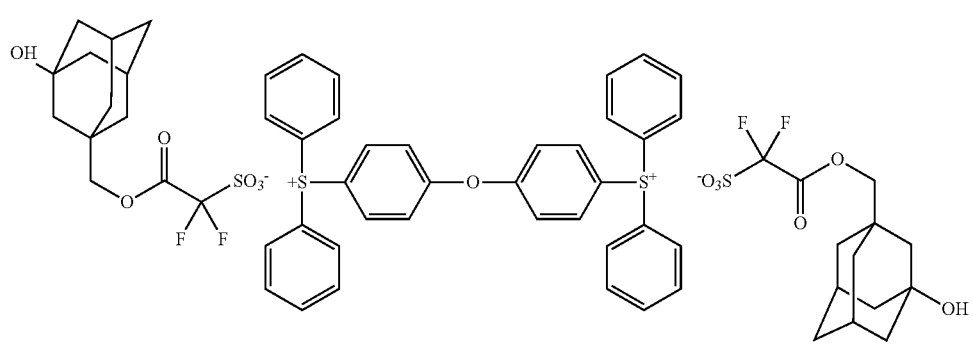
(B1-22)
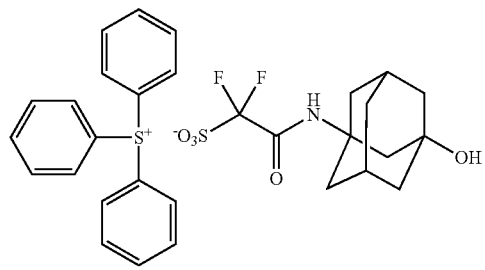
(B1-23)
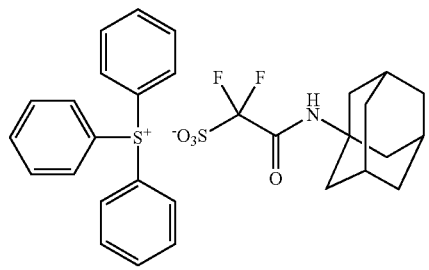
(B1-24)
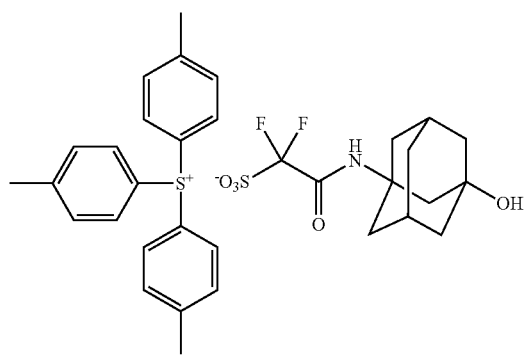
(B1-25)
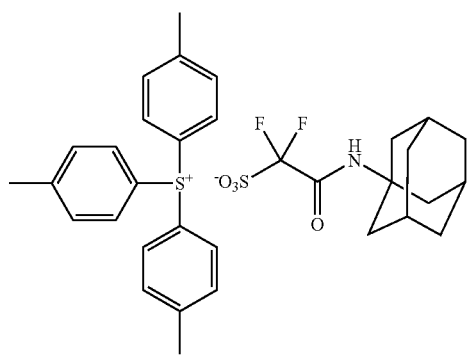

-continued

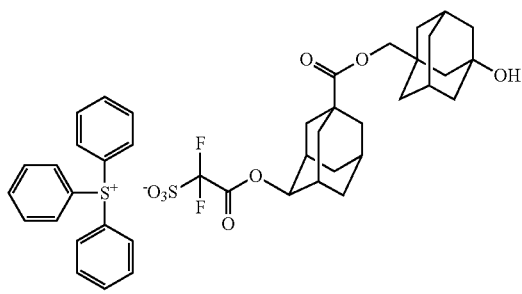
(B1-26)

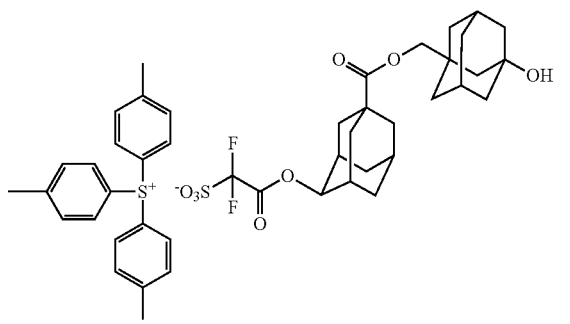
(B1-27)

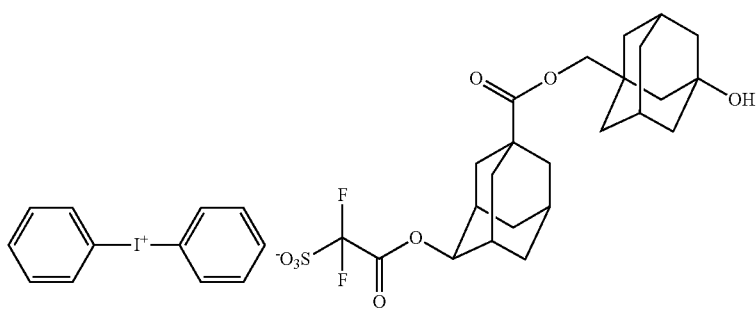
(B1-28)

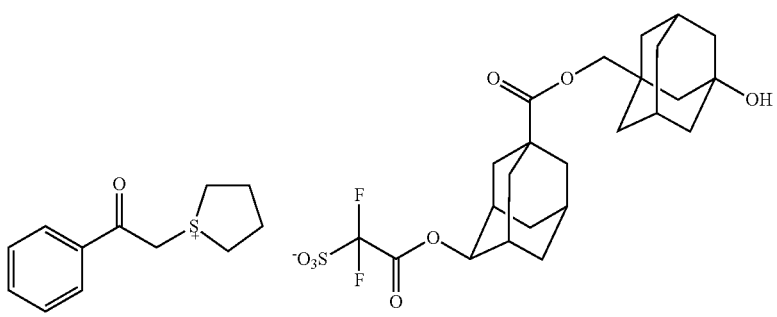
(B1-29)

Among the salt represented by the formula (I), a salt represented by the formula (G):

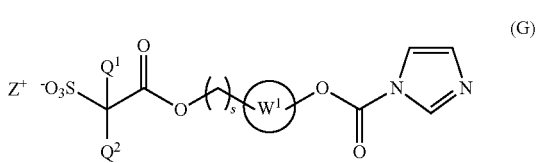
(G)

can be used as an acid generator for a photoresist composition. The photoresist composition containing the salt represented by the formula (G) gives a photoresist pattern having good line edge roughness.

wherein $Z^+$, $Q^1$ and $Q^2$ are the same as defined above, and ring $W^1$ represents a C3-C20 hydrocarbon ring which can have one or more substituents selected from the group consisting of a hydroxyl group, a C1-C6 alkyl group, a C1-C6 alkoxy group, a C3-C12 alicyclic hydrocarbon group and a C6-C10 aromatic hydrocarbon group, and represents an integer of 0 to 6.

Examples of the C3-C20 hydrocarbon ring include an adamantane ring, a cyclohexane ring and a norbornane ring, and an adamantane ring is preferable.

Examples of the C1-C6 alkyl group, the C1-C6 alkoxy group, the C3-C12 alicyclic hydrocarbon group and the C6-C10 aromatic hydrocarbon group include the same as described above, respectively.

Examples of the salt represented by the formula (G) include the following.
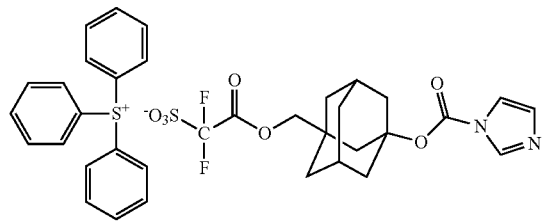
(G-1)
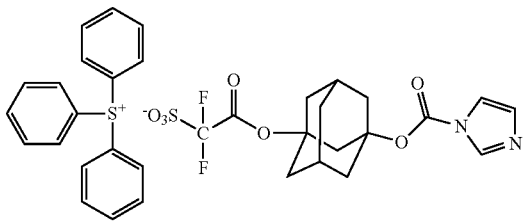
(G-2)
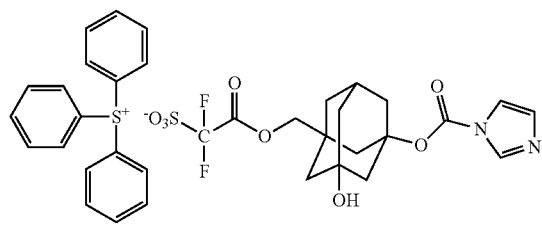
(G-3)
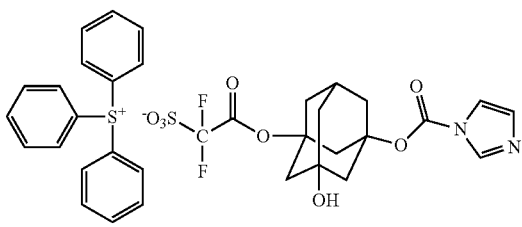
(G-4)
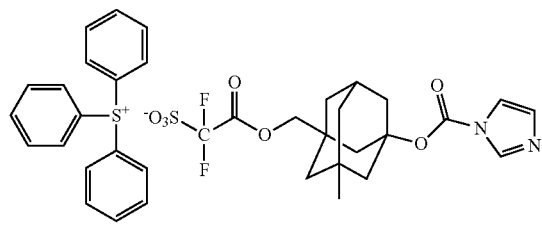
(G-5)
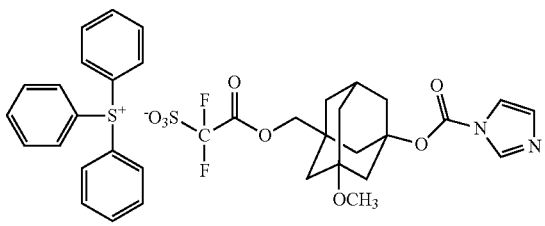
(G-6)
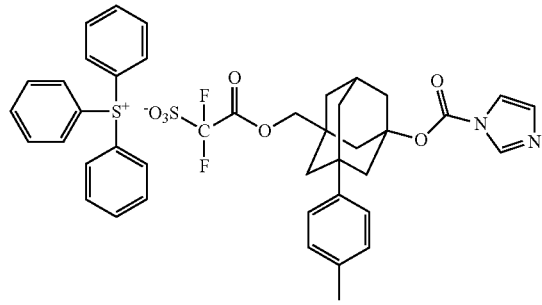
(G-7)
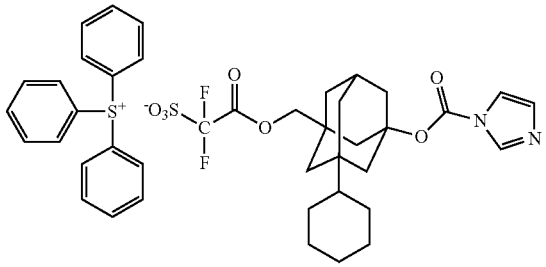
(G-8)
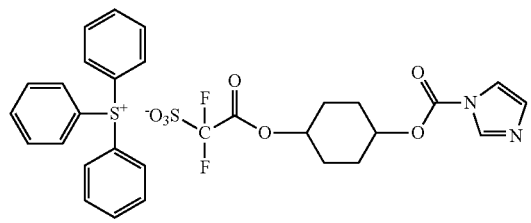
(G-9)
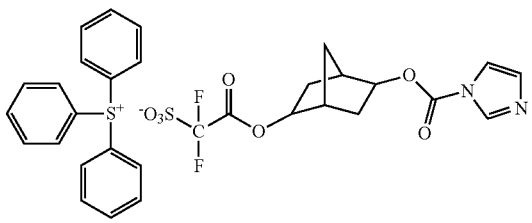
(G-10)

-continued
(G-11)
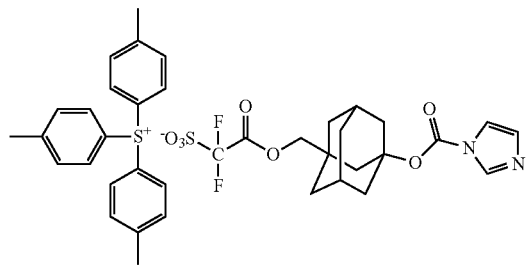
(G-12)
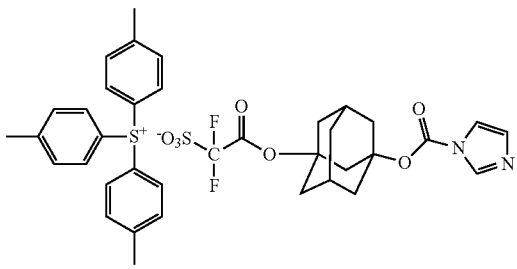
(G-13)
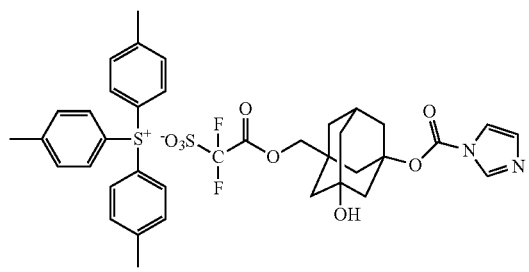
(G-14)
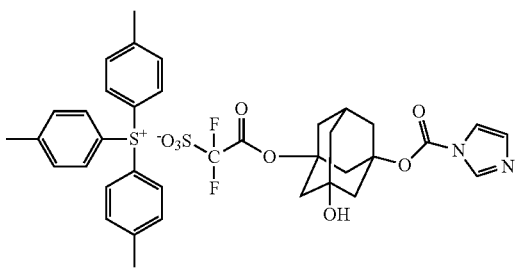
(G-15)
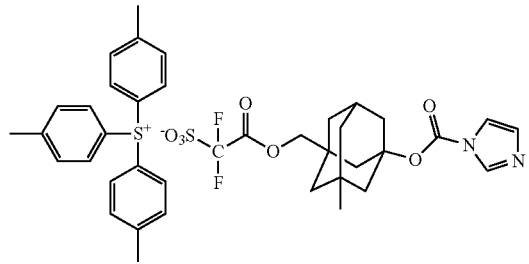
(G-16)
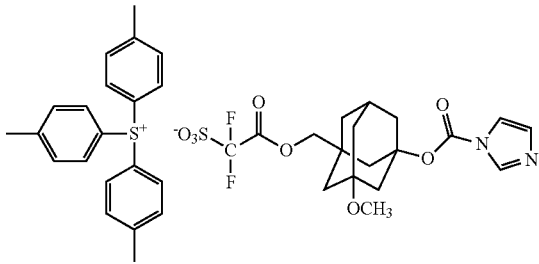
(G-17)
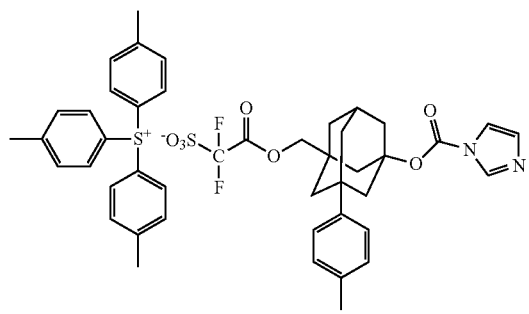
(G-18)
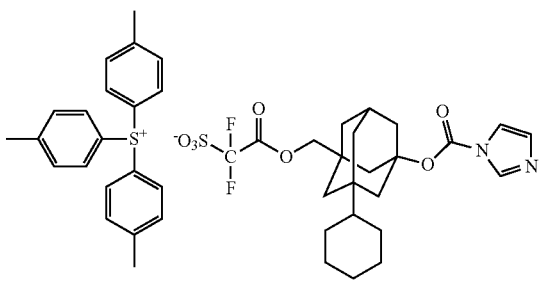
(G-19)
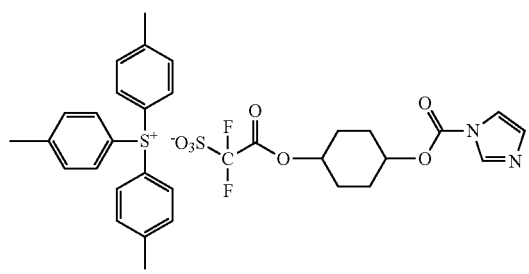
(G-20)
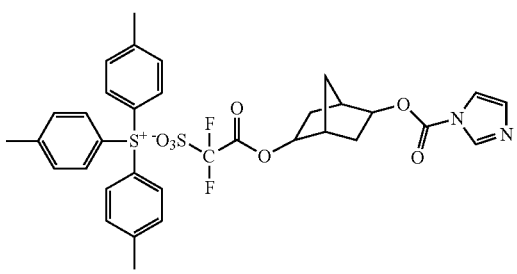
(G-21)
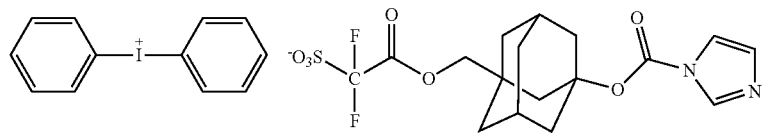

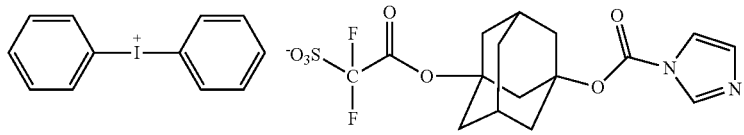
(G-22)
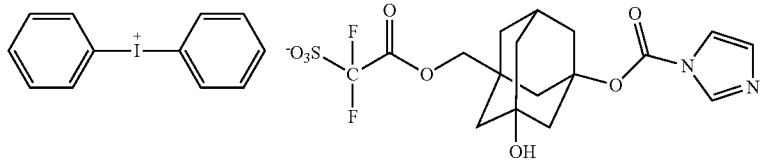
(G-23)
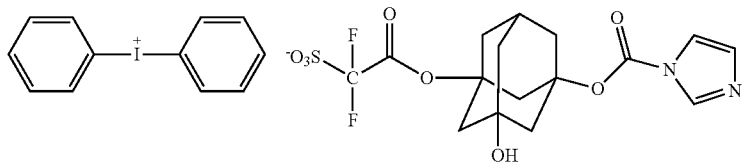
(G-24)
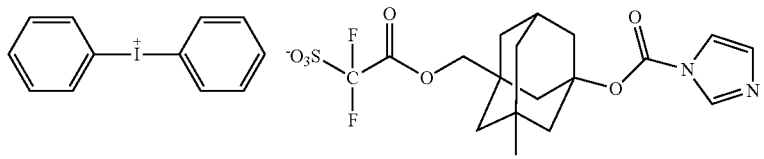
(G-25)
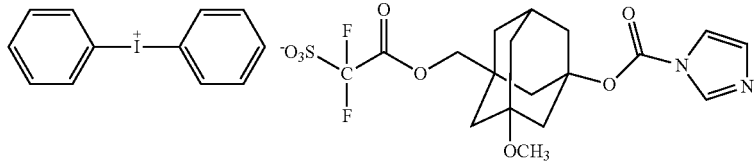
(G-26)
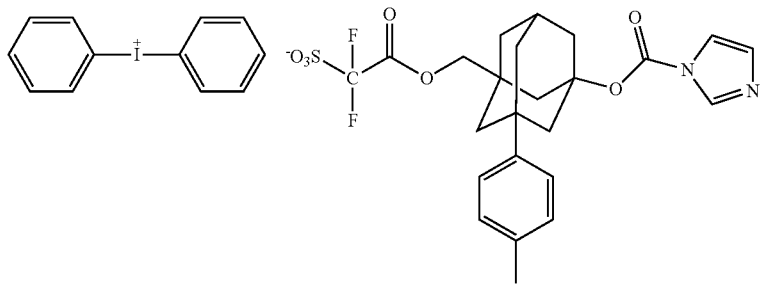
(G-27)
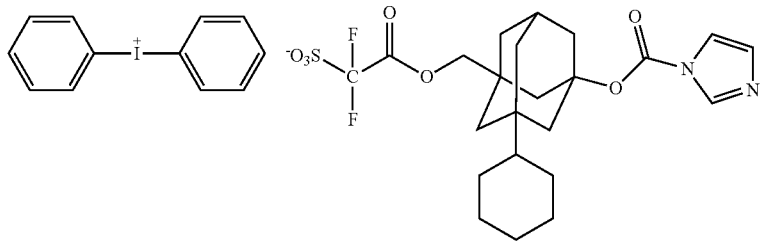
(G-28)
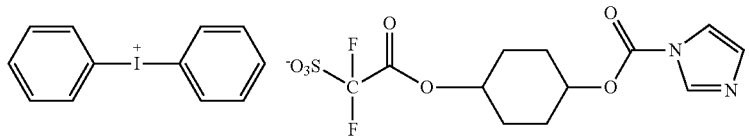
(G-29)

-continued
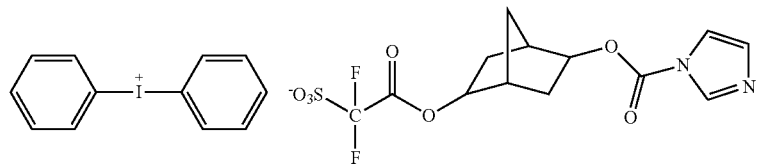
(G-30)
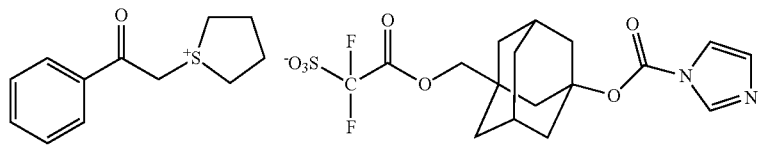
(G-31)
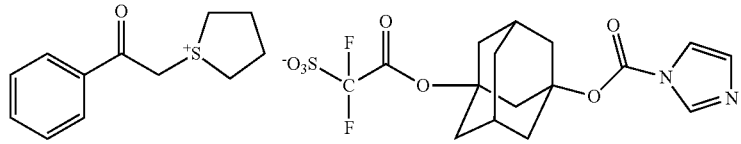
(G-32)
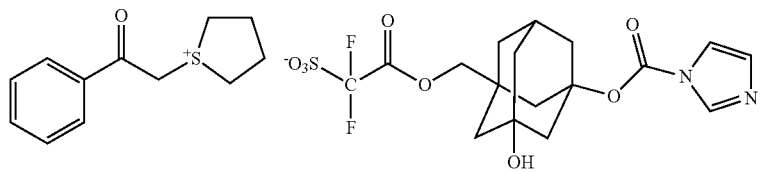
(G-33)
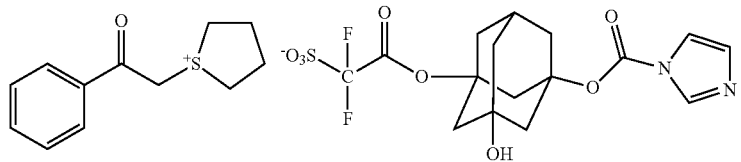
(G-34)
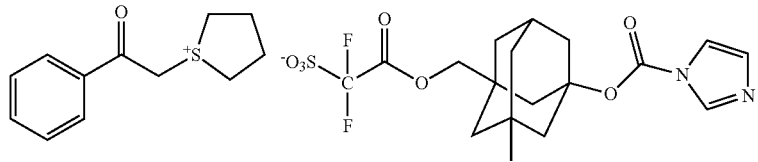
(G-35)
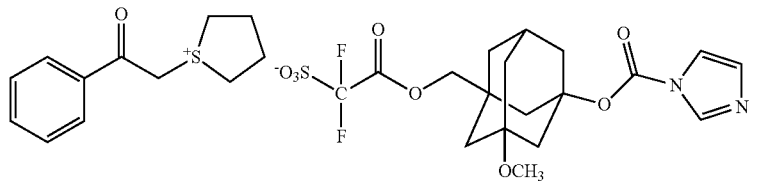
(G-36)
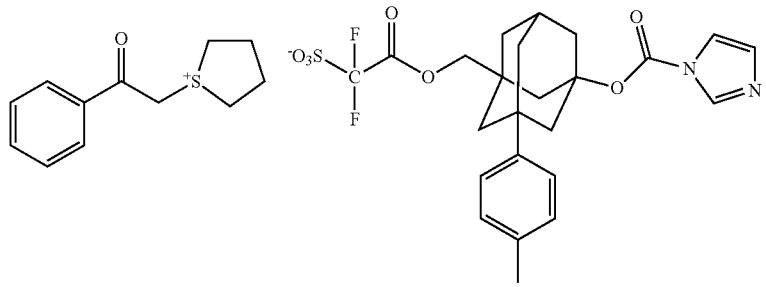
(G-37)

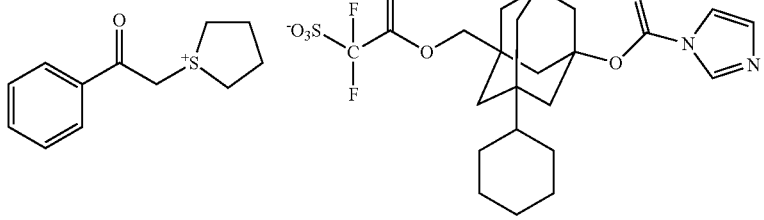
(G-38)

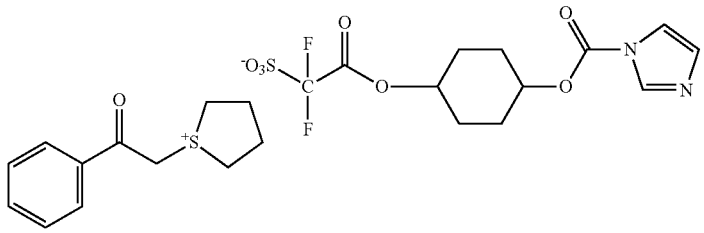
(G-39)

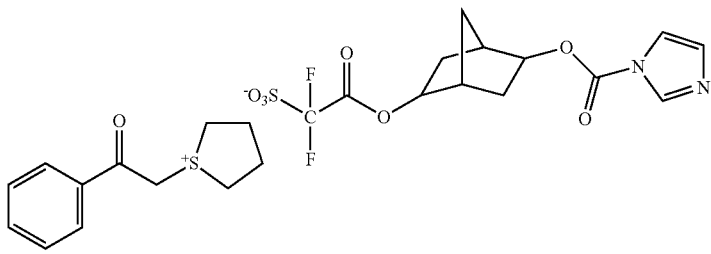
(G-40)

The salt represented by the formula (G) works as an acid generator in a photoresist composition. The acid generator is a substance which is decomposed to generate an acid by applying a radiation such as a light, an electron beam or the like on the substance itself or on a resist composition containing the substance. The acid generated from the salt of the present invention acts on a resin in a photoresist composition resulting in cleavage of the acid-labile group existing in the resin.

The photoresist composition of the present invention comprises a salt represented by the formula (G) and a resin comprising a structural unit having an acid-labile group and being insoluble or poorly soluble in an aqueous alkali solution but becoming soluble in an aqueous alkali solution by the action of an acid. The photoresist composition can contain one or more acid generators other than the salt represented by the formula (G).

In this specification, "an acid-labile group" means a group capable of being eliminated by the action of an acid.

Examples of the acid-labile group include a group represented by the formula (1a):

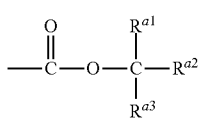
(1a)

wherein $R^{a1}$, $R^{a2}$ and $R^{a3}$ independently each represent a C1-C8 alkyl group or a C3-C20 alicyclic hydrocarbon group, or $R^{a1}$ and $R^{a2}$ are bonded each other to form a C3-C20 ring, and a group represented by the formula (2a):

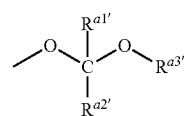
(2a)

wherein $R^{a1'}$ and $R^{a2'}$ independently each represent a hydrogen atom or a C1-C12 hydrocarbon group, and $R^{a3'}$ represents a C1-C20 hydrocarbon group or $R^{a2'}$ and $R^{a3'}$ are bonded each other to form a C2-C20 divalent hydrocarbon group in which one or more —$CH_2$— can be replaced by —O— or —S—.

Examples of the C1-C8 alkyl group include a methyl group, an ethyl group, a propyl group, an isopropyl group, a butyl group, a pentyl group, a hexyl group, a heptyl group and an octyl group.

The C3-C20 alicyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

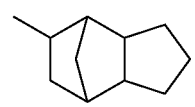 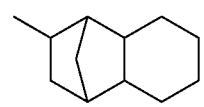

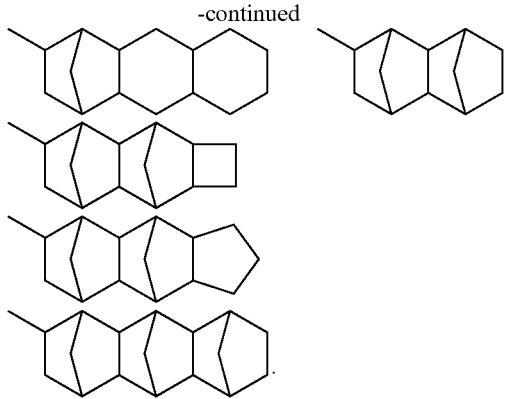

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

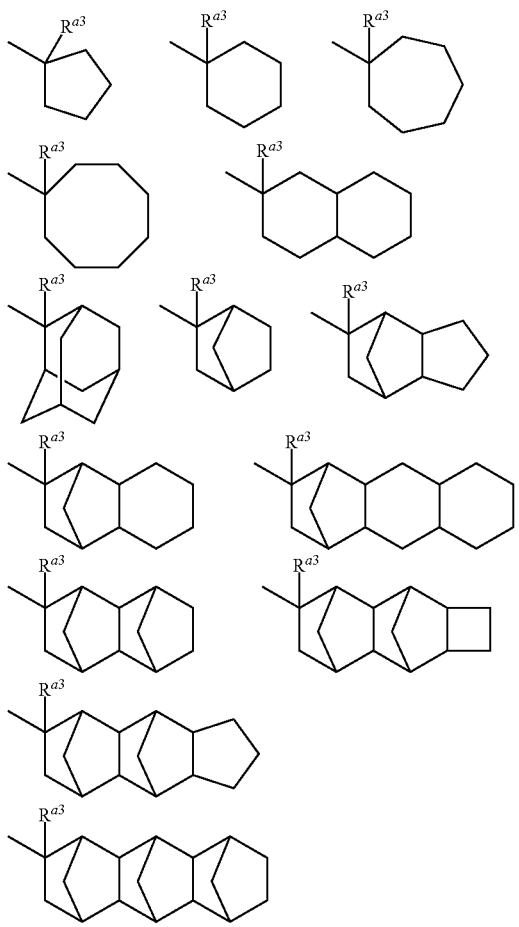

wherein $R^{a3}$ is the same as defined above.

The group represented by the formula (1a) wherein $R^{a1}$, $R^{a2}$ and $R^{a3}$ independently each represent a C1-C8 alkyl group such as a tert-butyl group, the group represented by the formula (1a) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1a) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

Examples of the hydrocarbon group represented by $R^{a1'}$, $R^{a2'}$ and $R^{a3'}$ include an alkyl group, an alicyclic hydrocarbon group and an aromatic hydrocarbon group. Examples of the alkyl group and the alicyclic hydrocarbon group include the same as described above, respectively. Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

At least one selected from the group consisting of $R^{a1'}$ and $R^{a2'}$ is preferably a hydrogen atom.

Examples of the group represented by the formula (2a) include the following.

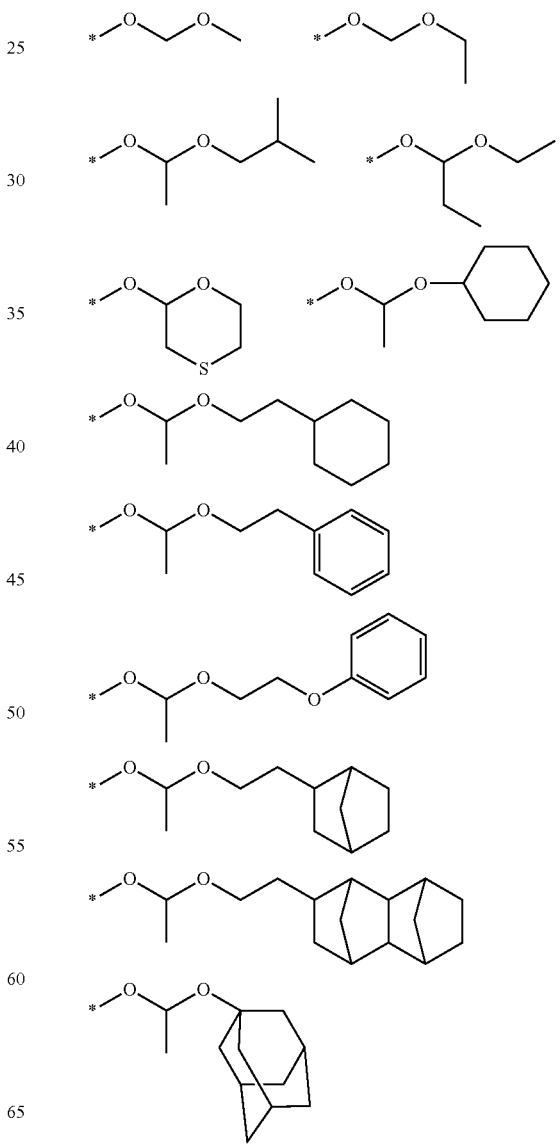

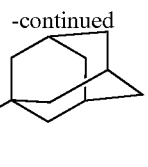

wherein * represents a binding position to a neighboring carbon atom.

The structural unit having an acid-labile group is derived from a monomer having an acid-labile group in its side chain and a carbon-carbon double bond, and an acrylate monomer having an acid-labile group in its side chain or a methacryalte monomer having an acid-labile group in its side chain is preferable.

Preferable examples of the compound having an acid-labile group include monomers represented by the formulae (a1-1) and (a1-2):

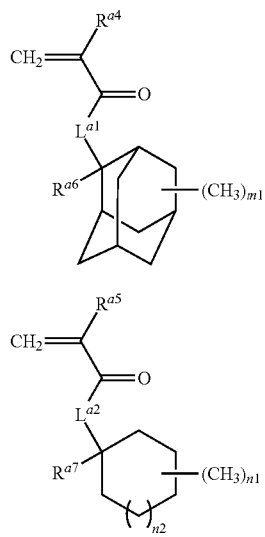

wherein $R^{a4}$ and $R^{a5}$ independently represent a hydrogen atom or a methyl group, $R^{a6}$ and $R^{a7}$ independently represents a C1-C8 alkyl group or a C3-C10 alicyclic hydrocarbon group, $L^{a1}$ and $L^{a2}$ independently represent *—O— or *—O—$(CH_2)_{k1}$—CO—O— in which * represents a binding position to —CO—, and k1 represents an integer of 1 to 7, m1 represents an integer of 0 to 14, n1 represents an integer of 0 to 10 and n2 represents 0 or 1.

The alkyl group preferably has 1 to 6 carbon atoms, and the alicyclic hydrocarbon group preferably has 3 to 8 carbon atoms and more preferably 3 to 6 carbon atoms.

Examples of the alkyl group include a methyl group, an ethyl group, a propyl group, an isopropyl group, a butyl group, a pentyl group, a hexyl group, a heptyl group and an octyl group. Examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic saturated hydrocarbon group such as a decahydronaphthyl group, an adamantyl group, a norbornyl group, a methylnorbornyl group and the following.

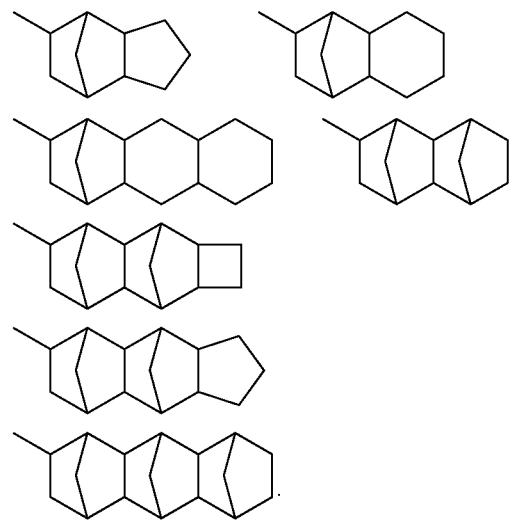

$L^{a1}$ is preferably *—O— or *—O—$(CH_2)_f$—CO—O— in which * represents a binding position to —CO—, and f represents an integer of 1 to 4, and is more preferably *—O— or *—O—$CH_2$—CO—O—, and is especially preferably *—O—.

$L^{a2}$ is preferably *—O— or *—O—$(CH_2)_f$—CO—O— in which * represents a binding position to —CO—, and f represents an integer of 1 to 4, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Examples of the monomer represented by the formula (a1-1) include the monomers described in JP 2010-204646 A. The monomers represented by the formulae (a1-1-1) to (a1-1-6) are preferable, and the monomers represented by the formulae (a1-1-1) to (a1-1-3) are more preferable.

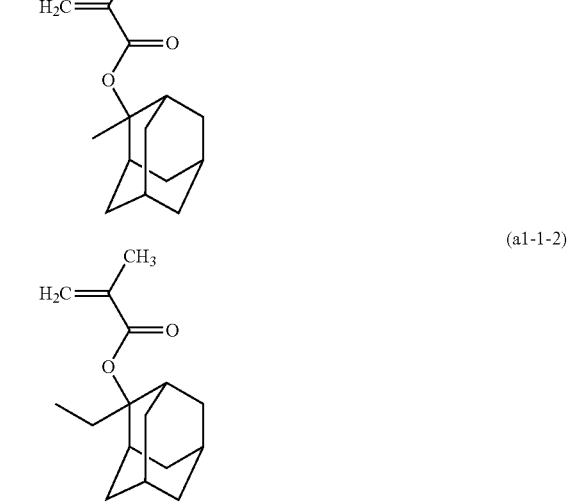

-continued

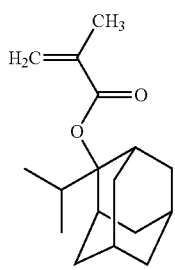
(a1-1-3)

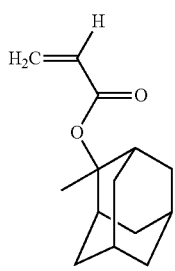
(a1-1-4)

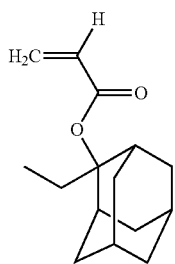
(a1-1-5)

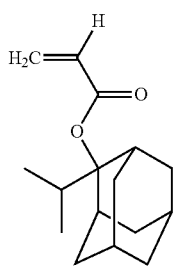
(a1-1-6)

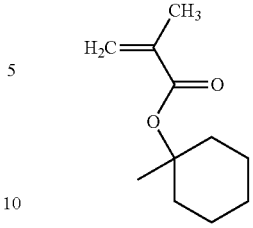
(a1-2-1)

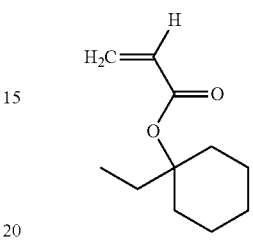
(a1-2-2)

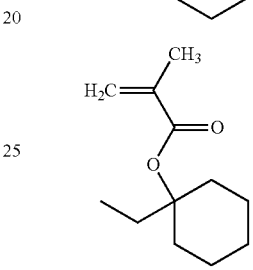
(a1-2-3)

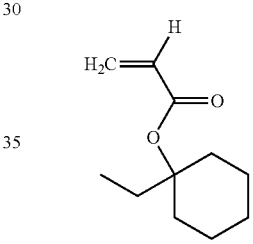
(a1-2-4)

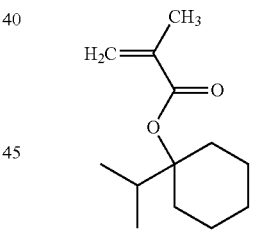
(a1-2-5)

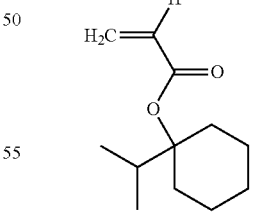
(a1-2-6)

Examples of the monomer represented by the formula (a1-2) include 1-ethyl-1-cyclopentyl acrylate, 1-ethyl-1-cyclopentyl methacrylate, 1-ethyl-1-cyclohexylacrylate, 1-ethyl-1-cyclohexyl methacrylate, 1-ethyl-1-cycloheptyl acrylate, 1-ethyl-1-cycloheptyl methacrylate, 1-methyl-1-cyclopentyl acrylate, 1-methyl-1-cyclopentyl methacrylate, 1-isopropyl-1-cyclopentyl acrylate and 1-isopropyl-1-cyclopentyl methacrylate. Among them, preferred are the monomers represented by the formulae (a1-2-1) to (a1-2-6), and more preferred are the monomers represented by the formulae (a1-2-3) and (a1-2-4), and especially preferred is the monomer represented by the formula (a1-2-3).

The content of the structural unit having an acid-labile group in the resin is usually 10 to 95% by mole based on total molar of all the structural units of the resin, preferably 15 to 90% by mole and more preferably 20 to 85% by mole.

The resin preferably contains one or more structural units having no acid-labile group in addition to the structural unit having an acid-labile group. The structural units having no acid-labile group can be derived from a monomer having no acid-labile group.

The resin can have two or more kinds of structural units derived from the monomers having no acid-labile group. When the resin contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1), in the structural units derived from the monomer having an acid-labile group is preferably 15% by mole or more from the viewpoint of dry-etching resistance of the photoresist composition.

The monomer having no acid-labile group preferably contains one or more hydroxyl groups or a lactone ring. When the resin contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

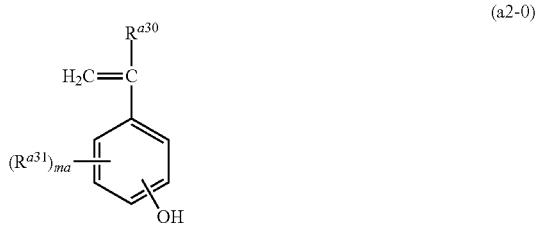

(a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, and ma represents an integer of 0 to 4, and a monomer represented by the formula (a2-1):

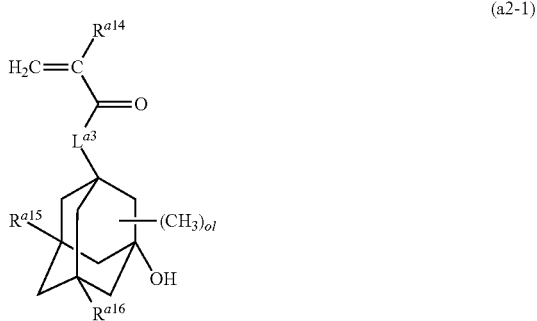

(a2-1)

wherein $R^{a14}$ represents a hydrogen atom or a methyl group, $R^{a15}$ and $R^{a16}$ independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

The monomer represented by the formula (a2-0) has a phenolic hydroxyl group.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) and the structural unit derived from the monomer having an acid-labile group can be produced, for example, by polymerizing the monomer having an acid-labile group and a monomer obtained by protecting a hydroxyl group of the monomer represented by the formula (a2-0) with an acetyl group followed by conducting deacetylation of the obtained polymer.

Examples of the monomer represented by the formula (a2-0) include the monomers described in JP 2010-204634 A. Among them, preferred are the monomers represented by the formulae (a2-0-1) and (a2-0-2).

(a2-0-1)

(a2-0-2)

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—(CH$_2$)$_{f2}$—CO—O— in which * represents a binding position to —CO—, and f2 represents an integer of 1 to 4, and is more preferably *—O—, and of is preferably 0, 1, 2 or 3 and is more preferably 0 or 1.

Examples of the monomer represented by the formula (a2-1) include the monomers described in JP 2010-204646 A. Among them, preferred are the monomers represented by the formulae (a2-1-1) to (a2-1-6), and more preferred are the monomer represented by the formulae (a2-1-1) to (a2-1-4) and especially preferred are the monomers represented by the formulae (a2-1-1) and (a2-1-3).

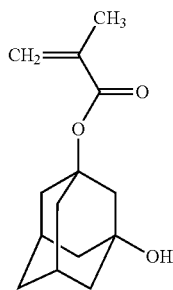

(a2-1-1)

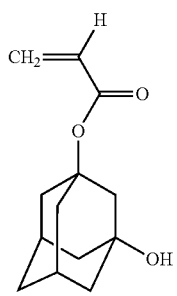

(a2-1-2)

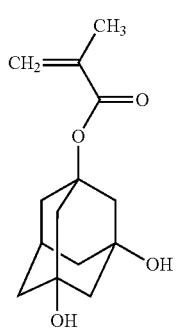

(a2-1-3)

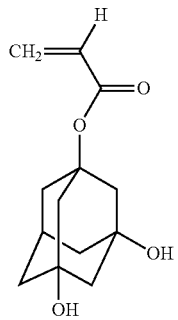

(a2-1-4)

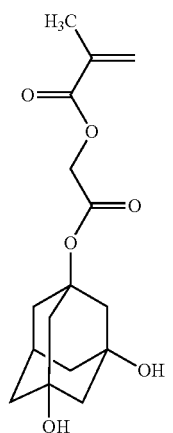

(a2-1-5)

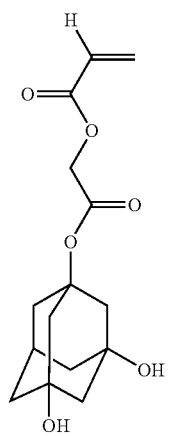

(a2-1-6)

When the resin contains the structural unit derived from the monomer represented by the formula (a2-1), the content of the structural unit derived from the monomer represented by the formula (a2-1) is usually 3 to 40% by mole and preferably 5 to 35% by mole and more preferably 5 to 30% by mole based on total molar of all the structural units of the resin.

Examples of the lactone ring of the monomer having no acid-labile group and having a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1) (a3-2) and (a3-3):

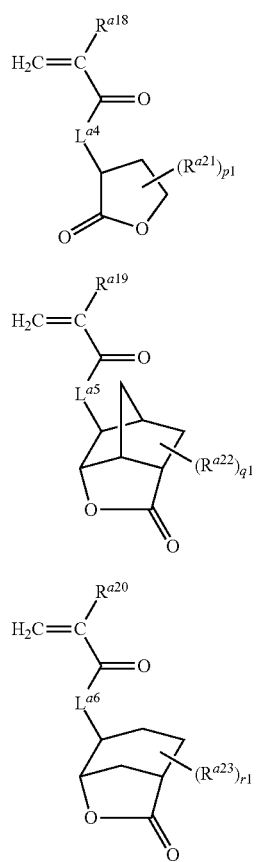

(a3-1)

(a3-2)

(a3-3)

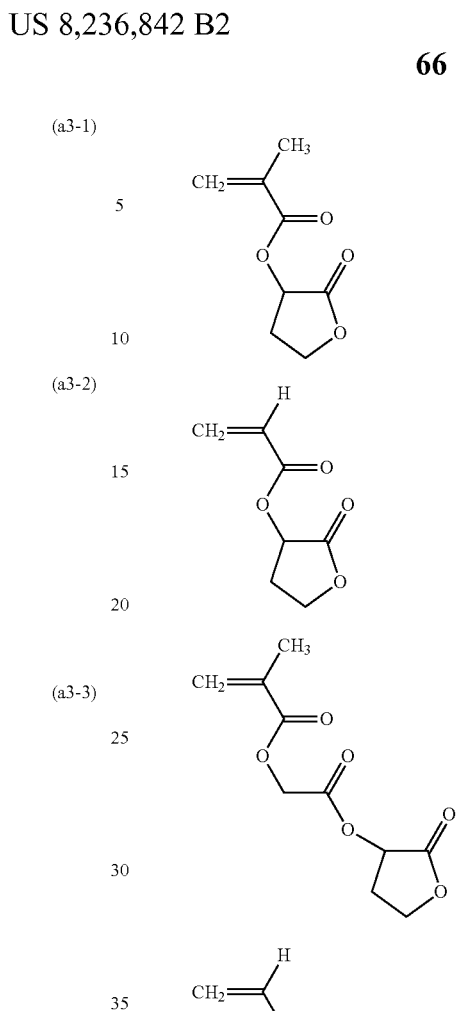

(a3-1-1)

(a3-1-2)

(a3-1-3)

(a3-1-4)

(a3-2-1)

(a3-2-2)

wherein $L^{a4}$, $L^{a5}$ and $L^{a6}$ independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ independently represent a hydrogen atom or a methyl group, $R^{a21}$ is independently in each occurrence a C1-C4 alkyl group, $R^{a22}$ and $R^{a23}$ are independently in each occurrence a carboxyl group, a cyano group or a C1-C4 alkyl group, and p1 represents an integer of 0 to 5, q1 and r1 independently represent an integer of 0 to 3.

It is preferred that $L^{a4}$, $L^{a5}$ and $L^{a6}$ are independently *—O— or *—O—$(CH_2)_{k4}$—CO—O— in which * represents a binding position to —CO— and k4 represents an integer of 1 to 4, it is more preferred that $L^{a4}$, $L^{a5}$ and $L^{a6}$ are independently *—O— or *—O—$CH_2$—CO—O— in which * represents a binding position to —CO—, and it is more especially preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomers represented by the formulae (a3-1), (a3-2) and (a3-3) include the monomers described in JP 2010-204646 A. Among them, preferred are the monomers represented by the formulae (a3-1-1) to (a3-1-4), (a3-2-1) to (a3-2-4) and (a3-3-1) to (a3-3-4), more preferred are the monomers represented by the formulae (a3-1-1) to (a3-1-2) and (a3-2-3) to (a3-2-4), and especially preferred are the monomers represented by the formulae (a3-1-1) and (a3-2-3).

(a3-2-3) 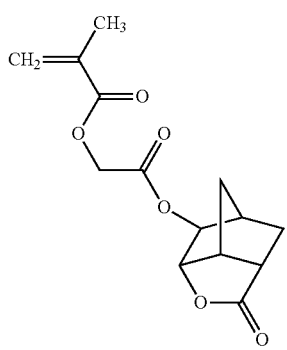

(a3-2-4) 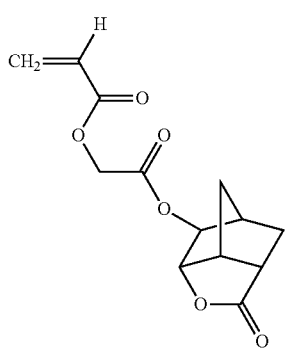

(a3-3-1) 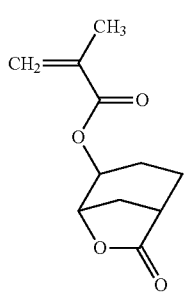

(a3-3-2) 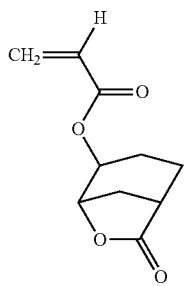

(a3-3-3) 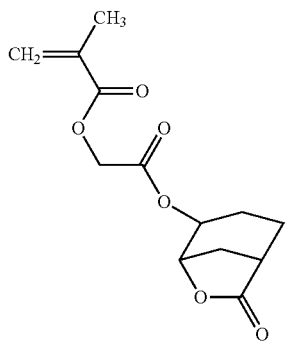

(a3-3-4) 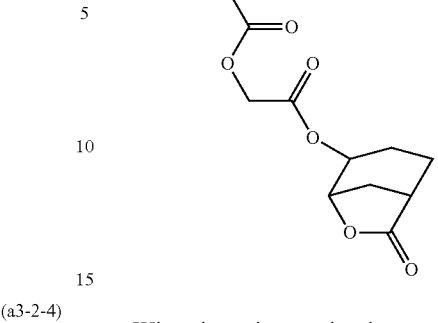

When the resin contains the structural unit derived from the monomer having no acid-labile group and having a lactone ring, the content thereof is usually 5 to 50% by mole and preferably 10 to 45% by mole and more preferably 15 to 40% by mole based on total molar of all the structural units of the resin.

The resin can have one or more structural units derived from the known monomers.

Preferable resin is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1).

The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, and preferably 3,000 or more of the weight-average molecular weight. The resin usually has 50,000 or less of the weight-average molecular weight, and preferably has 30,000 or less of the weight-average molecular weight. The weight-average molecular weight can be measured with gel permeation chromatography.

The content of the resin is usually 80% by weight or more in the solid component. In this specification, "solid component" means components other than solvents in the photoresist composition.

The content of the solid component can be analyzed with conventional means such as liquid chromatography and gas chromatography.

The photoresist composition contains one or more acid generators and examples thereof include the salt represented by the formula (B1) and the salt represented by the formula (G).

The amount of the acid generator in the photoresist composition is usually 1% by weight or more, and preferably 3% by weight or more based on the amount of the resin. The amount of the acid generator in the photoresist composition is usually 30% by weight or less, and preferably 25% by weight or less based on the amount of the resin.

In the photoresist composition, performance deterioration caused by inactivation of acid which occurs due to post exposure delay can be diminished by adding an organic base compound, particularly a nitrogen-containing organic base compound as a quencher.

Examples of the organic base compound include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include compounds represented by the formulae (C1), (C2), (C3), (C4), (C5), (C6), (C7) and (C8).

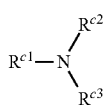
(C1)

wherein $R^{c1}$, $R^{c2}$ and $R^{c3}$ independently represent a hydrogen atom, a C1-6 alkyl group, a C5-C10 alicyclic hydrocarbon group or a C6-C10 aromatic hydrocarbon group, and the alkyl group and the alicyclic hydrocarbon group can have one or more substituents selected from the group consisting of a hydroxyl group, an amino group and a C1-C6 alkoxy group, and the aromatic hydrocarbon group can have one or more substituents selected from the group consisting of a C1-C6 alkyl group, a C1-C6 alkoxy group, a C5-C10 alicyclic hydrocarbon group and a C6-C10 aromatic hydrocarbon group.

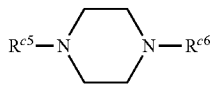
(C2)

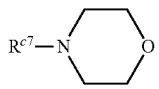
(C3)

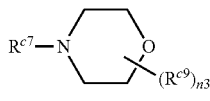
(C4)

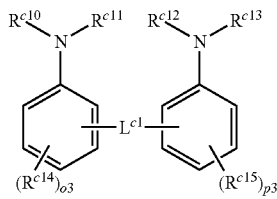
(C5)

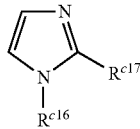
(C6)

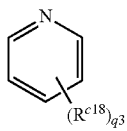
(C7)

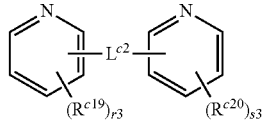
(C8)

wherein $R^{c5}$, $R^{c6}$, $R^{c7}$, $R^{a8}$, $R^{c10}$, $R^{c11}$, $R^{c12}$, $R^{c13}$ and $R^{c16}$ each independently represent a hydrogen atom, a C1-6 alkyl group, a C5-C10 alicyclic hydrocarbon group or a C6-C10 aromatic hydrocarbon group, and the alkyl group and the alicyclic hydrocarbon group can have one or more substituents selected from the group consisting of a hydroxyl group, an amino group and a C1-C6 alkoxy group, and the aromatic hydrocarbon group can have one or more substituents selected from the group consisting of a C1-C6 alkyl group, a C1-C6 alkoxy group, a C5-C10 alicyclic hydrocarbon group and a C6-C10 aromatic hydrocarbon group, $R^{c9}$ is independently in each occurrence a C1-C6 alkyl group, a C3-C6 alicyclic hydrocarbon group or a C2-C6 alkanoyl group, n3 represents an integer of 0 to 8, $R^{c14}$, $R^{c15}$, $R^{c17}$, $R^{c18}$, $R^{c19}$ and $R^{c20}$ each independently a C1-C6 alkyl group, a C1-C6 alkoxy group, a C5-C10 alicyclic hydrocarbon group or a C6-C10 aromatic hydrocarbon group, O3, p3, q3, r3 and s3 each independently represents an integer of 0 to 3 and n3 represents an integer of 0 to 8, $L^{c1}$ represents a C1-C6 alkanediyl group, —CO—, —C(=NH)—, —S— or a divalent group formed by combining two or more selected from a C1-C6 alkanediyl group, —CO—, —C(=NH)— and —S—, and $L^{c2}$ represents a single bond, a C1-C6 alkanediyl group, —CO—, —C(=NH)—, —S— or a divalent group formed by combining two or more selected from a C1-C6 alkanediyl group, —CO—, —C(=NH)— and —S—.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline.

Examples of the compound represented by the formula (C2) include piperazine. Examples of the compound represented by the formula (C3) include morpholine. Examples of the compound represented by the formula (C4) include piperidine and hindered amine compounds having a piperidine skeleton as disclosed in JP 11-52575 A. Examples of the compound represented by the formula (C5) include 2,2'-methylenebisaniline. Examples of the compound represented by the formula (C6) include imidazole and 4-methylimidazole. Examples of the compound represented by the formula (C7) include pyridine and 4-methylpyridine. Examples of the compound represented by the formula (C8) include di(2-pyridyl) ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, (3-trifluoromethylphenyl) trimethylammonium hydroxide, tetrabutylammonium salicylate and (2-hydroxyethyl)trimethylammonium hydroxide (so-called "choline").

Among them, preferred is a compound represented by the formula (C1-1):

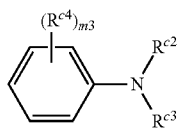

wherein $R^{c2}$ and $R^{c3}$ are the same as defined above, and $R^{c4}$ is independently in each occurrence a C1-C6 alkyl group, a C1-C6 alkoxy group, a C5-C10 alicyclic hydrocarbon group or a C6-C10 aromatic hydrocarbon group and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

When the basic compound is used, the amount of the basic compound is usually 0.01 to 5% by weight based on the amount of solid component, and preferably 0.01 to 3% by weight and more preferably 0.01 to 1% by weight.

The photoresist composition usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amounts of the photoresist composition.

The photoresist composition can contain, if necessary, a small amount of various additives such as a sensitizer, a dissolution inhibitor, other polymers, a surfactant, a stabilizer and a dye as long as the effect of the present invention is not prevented.

The photoresist composition is useful for a chemically amplified photoresist composition.

A photoresist pattern can be produced by the following steps (1) to (5):

(1) a step of applying the photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 µm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for ArF immersion lithography, EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. Structures of compounds were determined by mass spectrometry (Liquid Chromatography: 1100 Type, manufactured by AGILENT TECH- NOLOGIES LTD., Mass Spectrometry: LC/MSD Type or LC/MSD TOF Type, manufactured by AGILENT TECHNOLOGIES LTD.).

Example 1

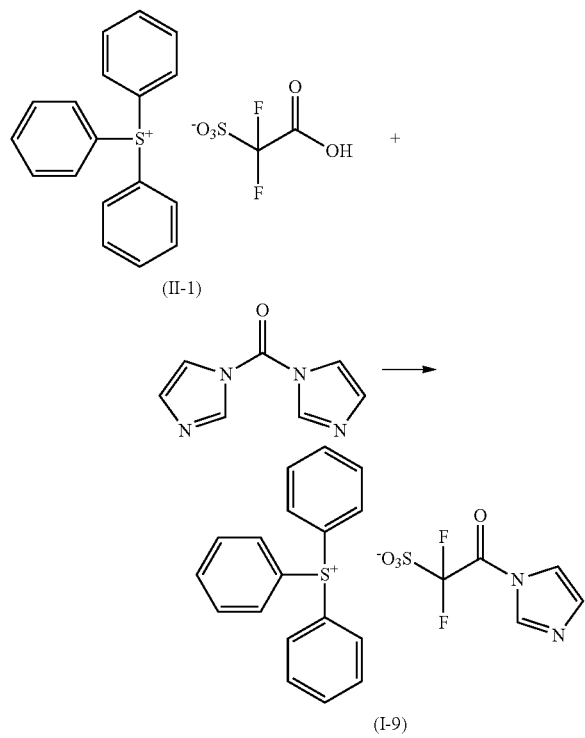

The salt represented by the formula (II-1) was prepared according to the method described in JP 2008-12767 A. A mixture of 59.76 parts of the salt represented by the formula (II-1), 300.00 parts of acetonitrile and 44.20 parts of carbonyldiimidazole which was available from Tokyo Chemical Industry Co., Ltd. was stirred at 23° C. for 30 minutes. The mixture was heated us to 50° C. and was further stirred at 50° C. for 2 hours. The mixture obtained was cooled down to 23° C. and then, filtrated to obtain 66.60 parts of the salt represented by the formula (I-9), which is called as Salt (I-9).

Yield: 100% based on the salt represented by the formula (II-1)

MS (ESI(+) Spectrum): M$^+$ 263.1
MS (ESI(−) Spectrum): M$^−$ 225.0

Example 2

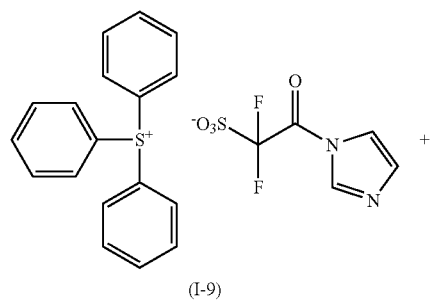

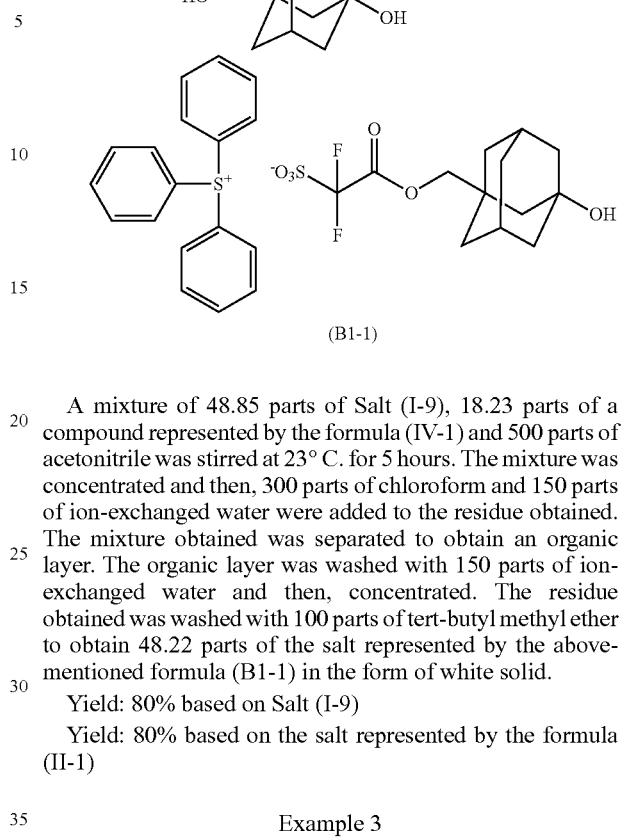

A mixture of 48.85 parts of Salt (I-9), 18.23 parts of a compound represented by the formula (IV-1) and 500 parts of acetonitrile was stirred at 23° C. for 5 hours. The mixture was concentrated and then, 300 parts of chloroform and 150 parts of ion-exchanged water were added to the residue obtained. The mixture obtained was separated to obtain an organic layer. The organic layer was washed with 150 parts of ion-exchanged water and then, concentrated. The residue obtained was washed with 100 parts of tert-butyl methyl ether to obtain 48.22 parts of the salt represented by the abovementioned formula (B1-1) in the form of white solid.

Yield: 80% based on Salt (I-9)
Yield: 80% based on the salt represented by the formula (II-1)

Example 3

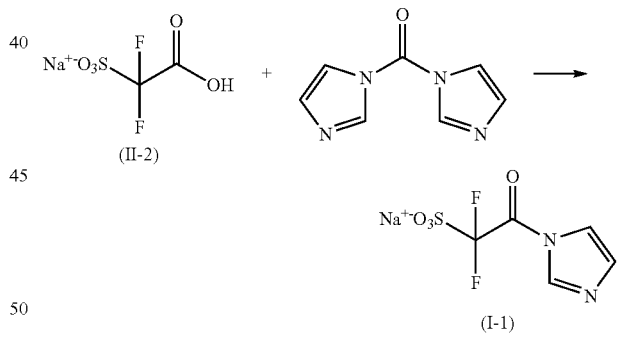

The salt represented by the formula (II-2) was prepared according to the method described in JP 2007-161707 A. A mixture of 19.81 parts of the salt represented by the formula (II-2), 100.00 parts of acetonitrile and 17.03 parts of carbonyldiimidazole which was available from Tokyo Chemical Industry Co., Ltd. was stirred at 23° C. for 30 minutes. The mixture was heated us to 50° C. and was further stirred at 50° C. for 2 hours. The mixture obtained was cooled down to 23° C. and then, filtrated to obtain 23.43 parts of the salt represented by the formula (I-1), which is called as Salt (I-1).

Yield: 94% based on the salt represented by the formula (II-2)

MS (ESI(+) Spectrum): M$^+$ 23.0
MS (ESI(−) Spectrum): M$^−$ 225.0

Example 4

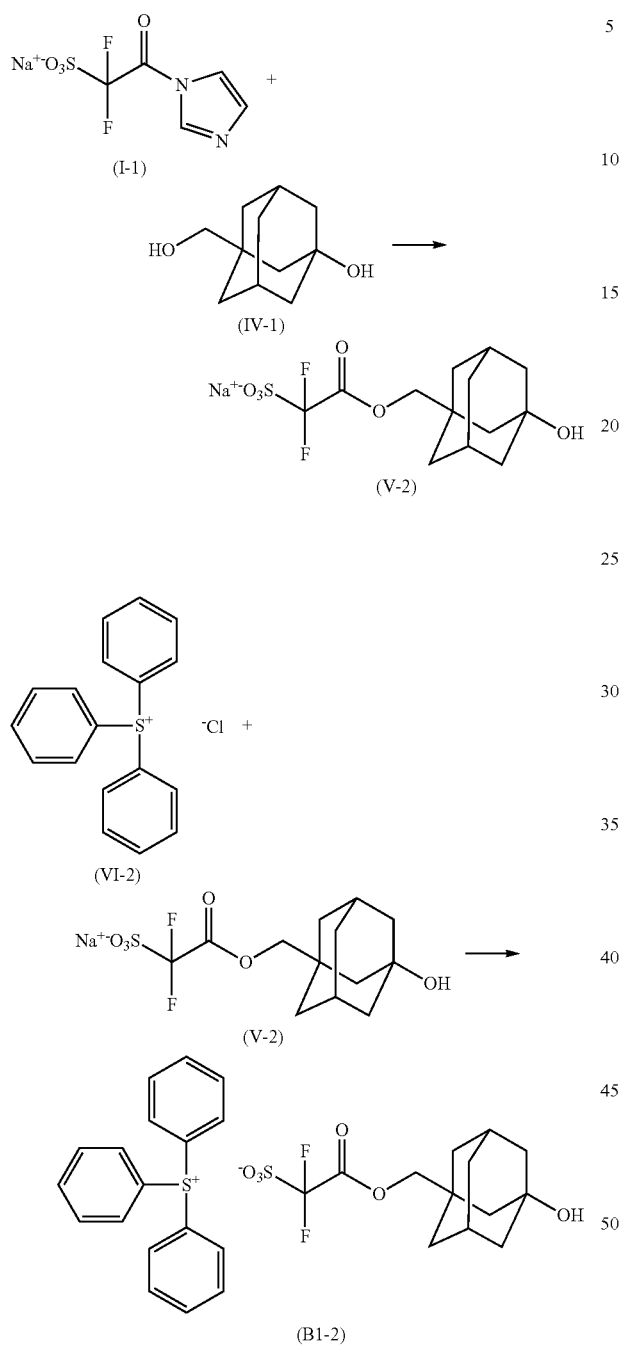

A mixture of 12.41 parts of Salt (I-1), 9.11 parts of a compound represented by the formula (IV-1) and 100 parts of acetonitrile was stirred at 23° C. for 5 hours. The mixture was filtrated to obtain 16.39 parts of the salt represented by the above-mentioned formula (V-2).

Yield: 90% based on Salt (I-1)
Yield: 85% based on the salt represented by the formula (II-2)

A mixture of 13.48 parts of the salt represented by the formula (VI-2), 16.39 parts of a compound represented by the formula (V-2), 163.9 parts of acetonitrile and 67.40 parts of ion-exchanged water was stirred at 23° C. for 15 hours. The mixture was concentrated and then, extracted with 100 parts of chloroform. The organic layer obtained was concentrated. The residue obtained was washed with 100 parts of tert-butyl methyl ether to obtain 25.13 parts of the salt represented by the above-mentioned formula (B1-2).

Yield: 92% based on the salt represented by the formula (VI-2)
Yield: 79% based on the salt represented by the formula (II-2)

Example 5

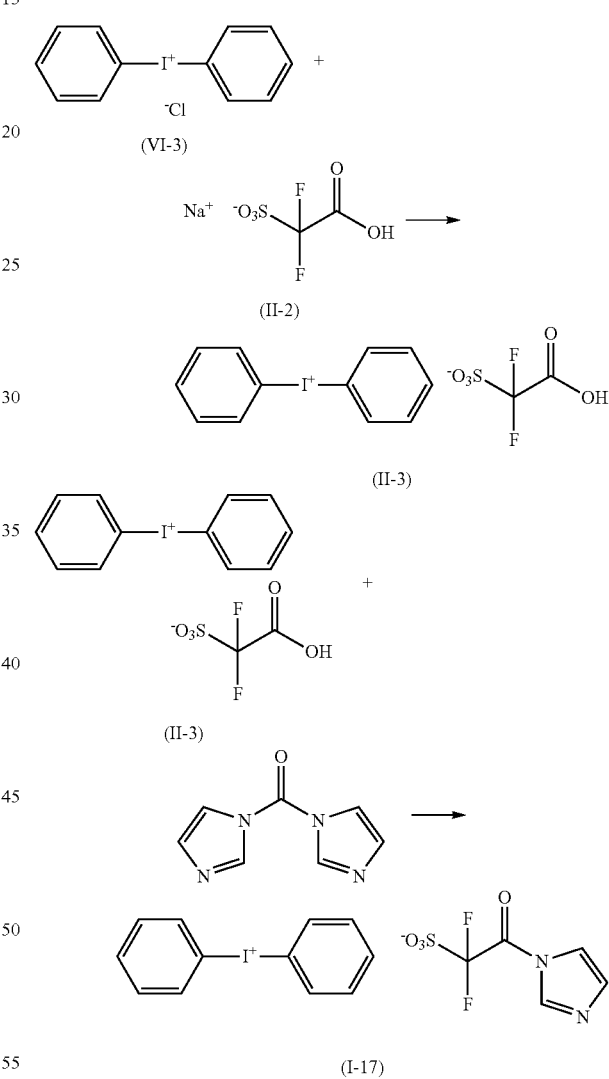

A mixture of 14.28 parts of a salt represented by the formula (VI-3), 8.96 parts of a salt represented by the formula (II-2), 100 parts of acetonitrile and 50 parts of ion-exchanged water was stirred at 23° C. for 15 hours. The mixture was concentrated and then, the residue obtained was extracted with 100 parts of chloroform. The organic layer obtained was concentrated to obtain 19.30 parts of the salt represented by the above-mentioned formula (II-3).

A mixture of 15.55 parts of the salt represented by the formula (II-3), 100.00 parts of acetonitrile and 11.05 parts of carbonyldiimidazole which was available from Tokyo Chemical Industry Co., Ltd. was stirred at 23° C. for 30 minutes. The mixture was heated us to 50° C. and was further stirred at 50° C. for 2 hours. The mixture obtained was cooled down to 23° C. and then, filtrated to obtain 17.25 parts of the salt represented by the formula (I-17), which is called as Salt (I-17).

MS (ESI(+) Spectrum): M+ 281.0
MS (ESI(−) Spectrum): M− 225.0

Example 6

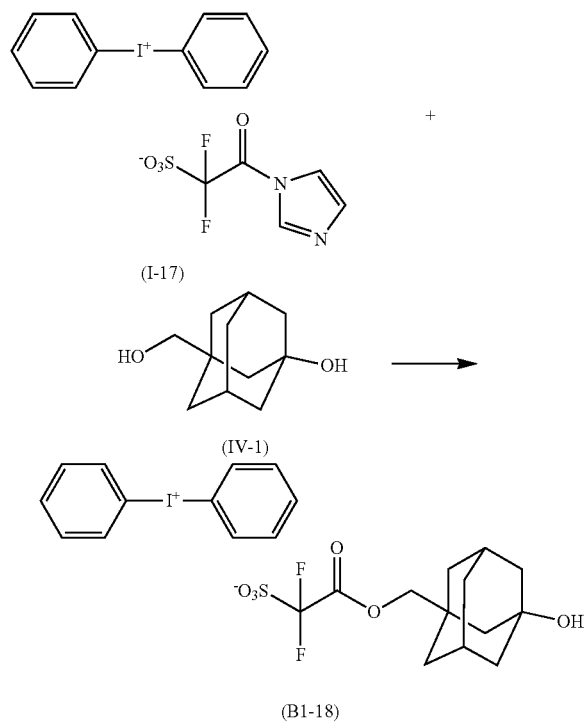

A mixture of 5.06 parts of Salt (I-17), 1.82 parts of a compound represented by the formula (IV-1) and 50 parts of acetonitrile was stirred at 23° C. for 5 hours. The mixture was concentrated and then, 30 parts of chloroform and 15 parts of ion-exchanged water were added to the residue obtained. The mixture obtained was separated to obtain an organic layer. The organic layer was washed with 15 parts of ion-exchanged water and then, concentrated. The residue obtained was washed with 10 parts of tert-butyl methyl ether to obtain 5.33 parts of the salt represented by the above-mentioned formula (B1-18) in the form of white solid.

Yield: 86% based on Salt (I-17)
Yield: 86% based on the salt represented by the formula (II-3)

Example 7

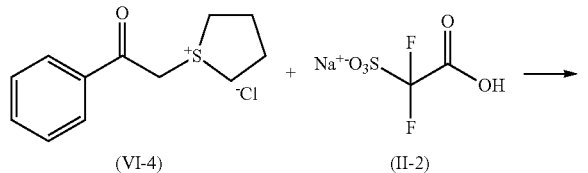

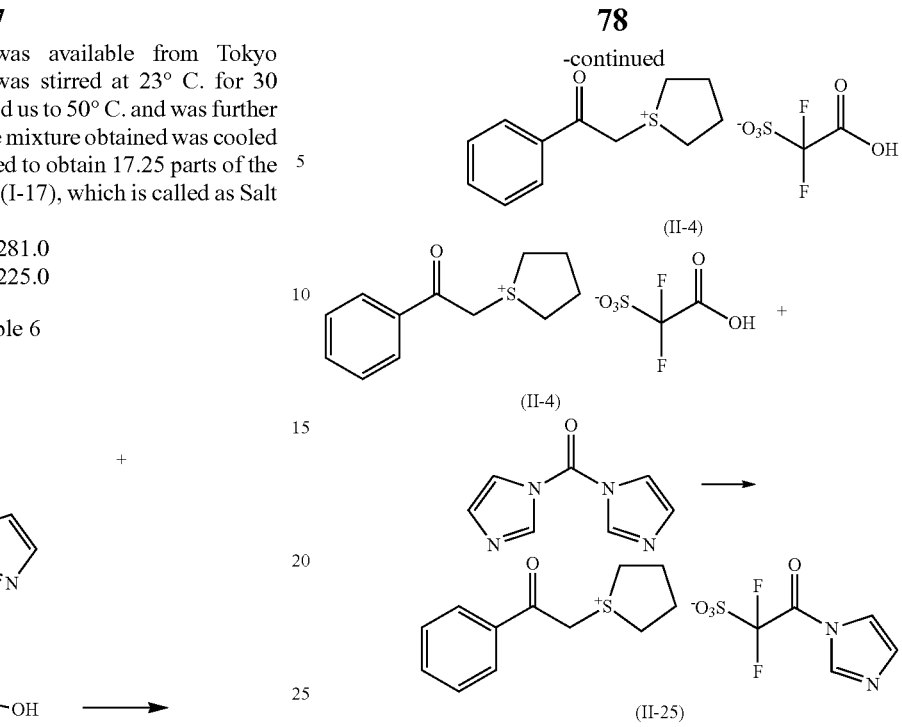

A mixture of 10.95 parts of a salt represented by the formula (VI-4), 8.96 parts of a salt represented by the formula (II-2), 100 parts of acetonitrile and 50 parts of ion-exchanged water was stirred at 23° C. for 15 hours. The mixture was concentrated and then, the residue obtained was extracted with 100 parts of chloroform. The organic layer obtained was concentrated to obtain 14.63 parts of the salt represented by the above-mentioned formula (II-4).

A mixture of 13.03 parts of the salt represented by the formula (VI-4), 100.00 parts of acetonitrile and 11.05 parts of carbonyldiimidazole which was available from Tokyo Chemical Industry Co., Ltd. was stirred at 23° C. for 30 minutes. The mixture was heated us to 50° C. and was further stirred at 50° C. for 2 hours. The mixture obtained was cooled down to 23° C. and then, filtrated to obtain 14.73 parts of the salt represented by the formula (I-25), which is called as Salt (I-25).

MS (ESI(+) Spectrum): M+ 207.1
MS (ESI(−) Spectrum): M− 225.0

Example 8

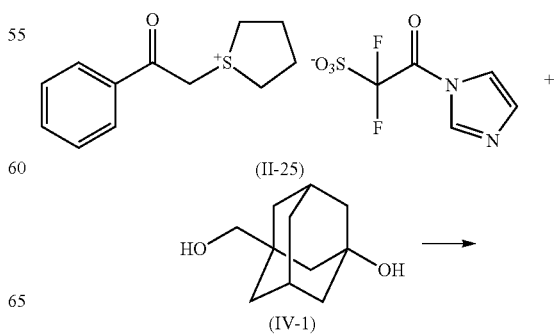

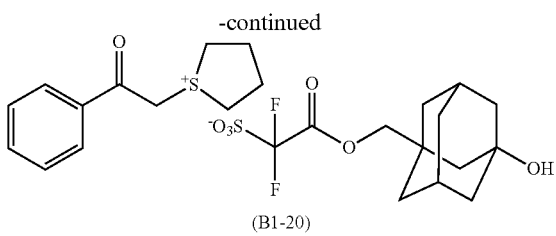

(B1-20)

A mixture of 4.32 parts of Salt (I-25), 1.82 parts of a compound represented by the formula (IV-1) and 50 parts of acetonitrile was stirred at 23° C. for 5 hours. The mixture was concentrated and then, 30 parts of chloroform and 15 parts of ion-exchanged water were added to the residue obtained. The mixture obtained was separated to obtain an organic layer. The organic layer was washed with 15 parts of ion-exchanged water and then, concentrated. The residue obtained was dissolved in 20 parts of acetonitrile, and the solution obtained was concentrated. To the residue, 20 parts of ethyl acetate was added. The mixture obtained was concentrated.

The residue obtained was mixed with 20 parts of tert-butyl methyl ether. The mixture obtained was stirred and then, the supernatant solution was removed. The residual layer was concentrated, and the residue obtained was mixed with 20 parts of ethyl acetate. The mixture obtained was stirred and the supernatant solution was removed. The residual layer was concentrated to obtain 4.27 parts of the salt represented by the formula (B1-20).

Yield: 78% based on Salt (I-25)

Yield: 78% based on the salt represented by the formula (II-4)

Example 9

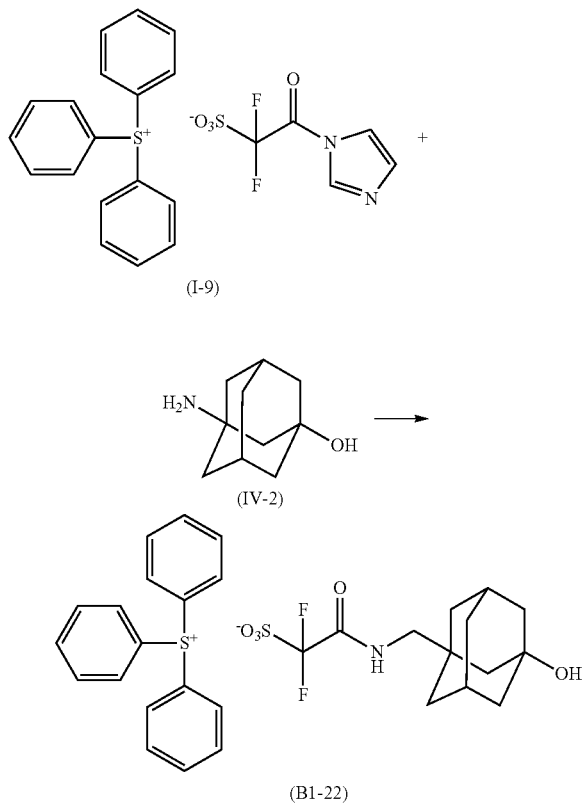

A mixture of 4.89 parts of Salt (I-9), 1.67 parts of a compound represented by the formula (IV-2) and 50 parts of acetonitrile was stirred at 23° C. for 5 hours. The mixture was concentrated and then, 30 parts of chloroform and 15 parts of ion-exchanged water were added to the residue obtained. The mixture obtained was separated to obtain an organic layer. The organic layer was washed with 15 parts of ion-exchanged water and then, concentrated. The residue obtained was dissolved in 20 parts of acetonitrile, and the solution obtained was concentrated. To the residue, 20 parts of ethyl acetate was added. The mixture obtained was concentrated.

The residue obtained was mixed with 20 parts of tert-butyl methyl ether. The mixture obtained was stirred and then, the supernatant solution was removed. The residual layer was concentrated, and the residue obtained was mixed with 20 parts of ethyl acetate. The mixture obtained was stirred and the supernatant solution was removed. The residual layer was concentrated to obtain 4.75 parts of the salt represented by the formula (B1-22).

Yield: 81% based on Salt (I-9)

Yield: 81% based on the salt represented by the formula (II-1)

Example 10

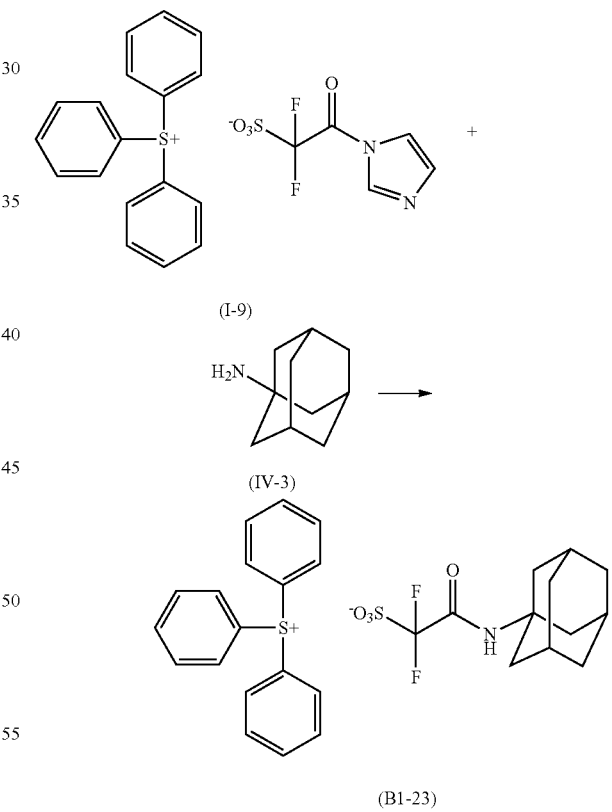

A mixture of 4.89 parts of Salt (I-9), 1.51 parts of a compound represented by the formula (IV-3) and 50 parts of acetonitrile was stirred at 23° C. for 5 hours. The mixture was concentrated and then, 30 parts of chloroform and 15 parts of ion-exchanged water were added to the residue obtained. The mixture obtained was separated to obtain an organic layer. The organic layer was washed with 15 parts of ion-exchanged water and then, concentrated. The residue obtained was dissolved in 20 parts of acetonitrile, and the solution obtained was concentrated. To the residue, 20 parts of ethyl acetate was added. The mixture obtained was concentrated.

The residue obtained was mixed with 20 parts of tert-butyl methyl ether. The mixture obtained was stirred and then, the supernatant solution was removed. The residual layer was concentrated, and the residue obtained was mixed with 20 parts of ethyl acetate. The mixture obtained was stirred and the supernatant solution was removed. The residual layer was concentrated to obtain 4.92 parts of the salt represented by the formula (B1-23).

Yield: 86% based on Salt (I-9)
Yield: 86% based on the salt represented by the formula (II-1)

Example 11

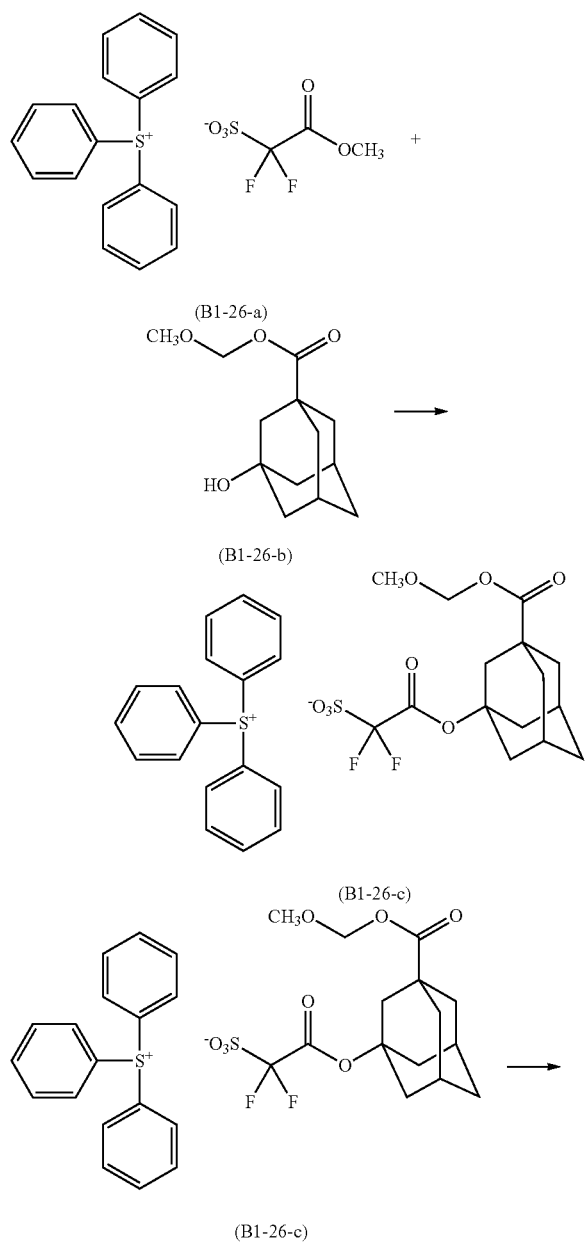

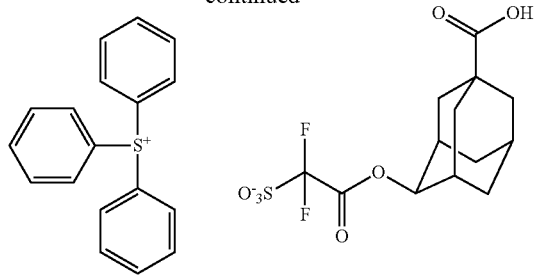

(B1-26-d)

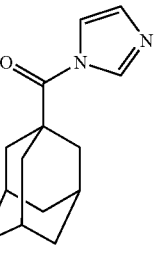

(B1-26-d)

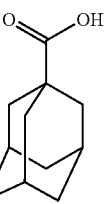

(I-33)

To a mixture of 10.00 parts of the salt represented by the formula (B1-26-a) and 80.00 parts of chloroform, 7.97 parts of a compound represented by the formula (B1-26-b) of which purity was 97.1% was added, and then, 0.15 part of lithium amide was added thereto. The resultant mixture was stirred at 23° C. for 30 minutes.

To the mixture obtained, 13.00 parts of molecular sieves (Molecular Sieves 5A available from Wako Pure Chemical Industries, Ltd.) was added, and then, the resultant mixture was stirred at 60° C. for 8 hours. The obtained mixture was cooled down to 23° C., and filtrated.

The filtrate obtained was washed with 24.53 parts of ion-exchanged water. The organic layer obtained was repeated twice to wash. To the organic layer, 1.33 parts of active carbon was added to stir followed by filtration. The filtrate obtained was concentrated to obtain 20.20 parts of an oily matter having pale yellow color.

The oily matter was dissolved in 60.60 parts of acetonitrile, and the solution obtained was concentrated. To the residue obtained, 81.80 parts of ethyl acetate was added to prepare a solution. The solution obtained was concentrated, and 76.60 parts of methyl tert-butyl ether was added to the obtained residue. The resultant mixture was stirred and then, the supernatant solution was removed from the mixture. The residual layer was concentrated, and to the residue obtained, 66.00 parts of ethyl acetate was added. The resultant mixture was stirred and then, the supernatant solution was removed from the mixture. The residual layer was concentrated to obtain 11.96 parts of a salt represented by the formula (B1-26-c).

A mixture prepared by mixing 6.60 parts of the salt represented by the formula (B1-26-c), 40.00 parts of chloroform and a mixed solution of 7.70 parts of 1N hydrochloric acid and 7.70 parts of methanol was stirred at 23° C. for 15 hours. To the mixture obtained, 40.00 parts of 1N aqueous sodium hydrogen carbonate solution was added, and the resultant mixture was mixed and separated. The organic layer was washed with 40.00 parts of ion-exchanged water. The organic layer was washed three times with ion-exchanged water. To the organic layer, 1.00 part of active carbon was added to stir followed by filtration. The filtrate obtained was concentrated to obtain 7.71 parts of a salt represented by the formula (B1-26-d).

A mixture of 7.00 parts of the salt represented by the formula (B1-26-d), 35 parts of acetonitrile and 2.21 parts of carbonyldiimidazole which was available from Tokyo Chemical Industry Co., Ltd. was stirred at 23° C. for 30 minutes. The mixture was heated us to 50° C. and was further stirred at 50° C. for 2 hours. The mixture obtained was cooled down to 23° C. and then, filtrated to obtain 6.94 parts of the salt represented by the formula (I-33), which is called as Salt (I-33).

MS (ESI(+) Spectrum): M$^+$ 263.1
MS (ESI(−) Spectrum): M$^-$ 403.1

Example 12

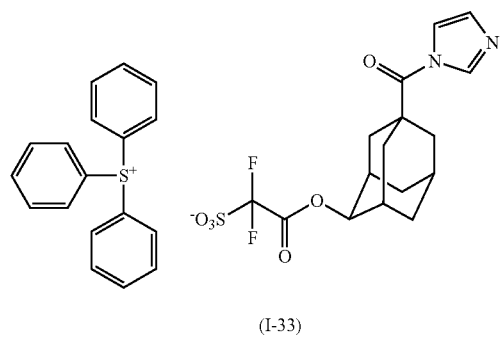

(I-33)

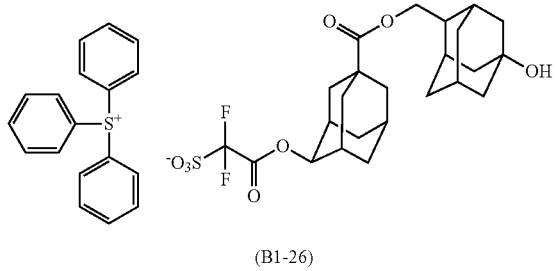

(B1-26)

A mixture of 6.67 parts of Salt (I-33), 1.82 parts of a compound represented by the formula (IV-1) and 50 parts of acetonitrile was stirred at 23° C. for 5 hours. The mixture was concentrated and then, 30 parts of chloroform and 15 parts of ion-exchanged water were added to the residue obtained. The mixture obtained was separated to obtain an organic layer. The organic layer was washed with 15 parts of ion-exchanged water and then, concentrated. The residue obtained was dissolved in 20 parts of acetonitrile, and the solution obtained was concentrated. To the residue, 20 parts of ethyl acetate was added. The mixture obtained was concentrated.

The residue obtained was mixed with 20 parts of tert-butyl methyl ether. The mixture obtained was stirred and then, the supernatant solution was removed. The residual layer was concentrated, and the residue obtained was mixed with 20 parts of ethyl acetate. The mixture obtained was stirred and the supernatant solution was removed. The residual layer was concentrated to obtain 6.42 parts of the salt represented by the formula (B1-26).

Yield: 82% based on Salt (I-26)
Yield: 75% based on the salt represented by the formula (B1-26-d)
MS (ESI(+) Spectrum): M$^+$ 263.1
MS (ESI(−) Spectrum): M$^-$ 517.2

Comparative Example 1

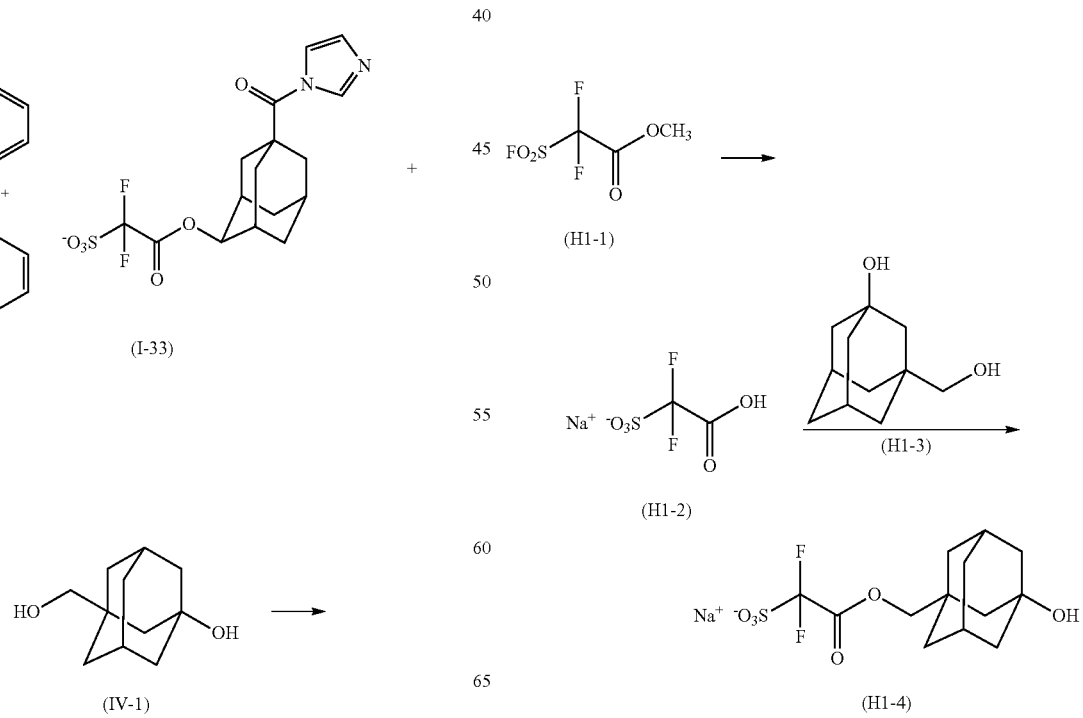

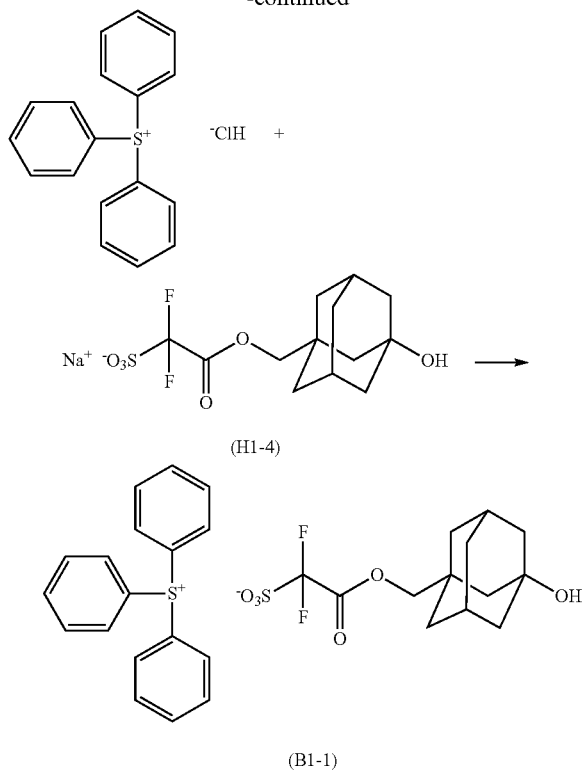

(H1-4)

(B1-1)

The salt represented by the formula (B1-1) was prepared as followed according to the method described in Example of JP 2006-257078 A.

To a mixture of 100 parts of a compound represented by the formula (H1-1) and 150 parts of ion-exchanged water, 230 parts of 30% aqueous sodium hydroxide solution was added dropwise under ice-bath. The resultant mixture was refluxed at 100° C. for 3 hours, and then, cooled. The mixture was neutralized with 88 parts of concentrated hydrochloric acid. The solution obtained was concentrated to obtain 164.4 parts of a salt represented by the formula (H1-2) of which purity was 92.7% and which contained inorganic salts. To a mixture of 1.9 parts of the salt represented by the formula (H1-2) which was obtained above and 9.5 parts of N,N-dimethylformamide, 1.0 part of carbonyldiimidazole was added, and the resultant mixture was stirred for 2 hours to prepare a solution containing the salt represented by the formula (H1-2).

To a mixture of 1.1 parts of a compound represented by the formula (H1-3) and 5.5 parts of N,N-dimethylformamide, 0.2 part of sodium hydride was added, and the resultant mixture was stirred for 2 hours. To the mixture obtained, the solution containing the salt represented by the formula (H1-2) was added. The resultant mixture was stirred for 15 hours to obtain a solution containing a salt represented by the formula (H1-4).

To the solution containing a salt represented by the formula (H1-4), 17.2 parts of chloroform and 2.9 parts of an aqueous solution containing a salt represented by the formula (H1-5) of which content was 14.8% were added. The resultant mixture was stirred for 15 hours, and then, separated to obtain an organic layer and an aqueous layer. The aqueous layer was repeated to extract with 6.5 parts of chloroform. The obtained organic layers were mixed and washed with ion-exchanged water. The organic layer was concentrated, and the residue was mixed with 5.0 parts of methyl tert-butyl ether.

The mixture obtained was stirred and filtrated to obtain 0.2 part of a salt represented by the formula (B1-1) in the form of white solid.

Yield: 23% based on the salt represented by the formula (H1-5)

Yield: 5.5% based on the salt represented by the formula (H1-2)

Yield: 5.5% based on the salt represented by the formula (H1-1)

Example 13

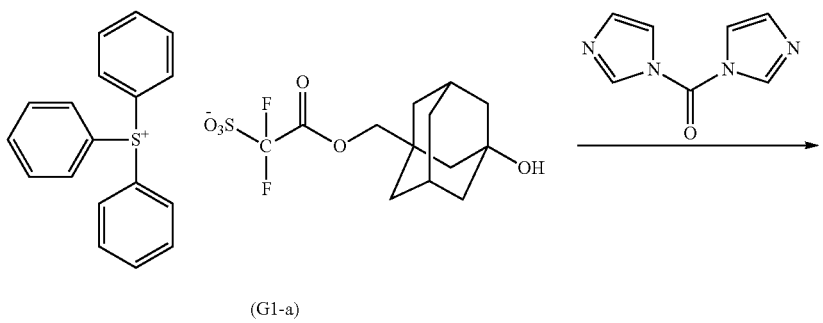

(G1-a)

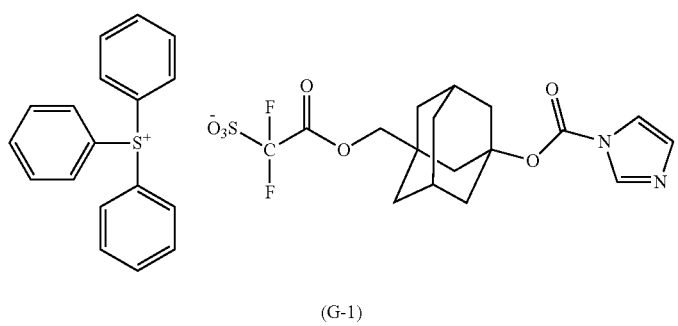

(G-1)

A mixture of 6.03 parts of the salt represented by the formula (G1-a) and 30.00 parts of acetonitrile was stirred at 23° C. for 30 minutes. To the mixture obtained, 1.70 parts of carbonyldiimidazole was added, and the resultant mixture was stirred at 60° C. for 1 hour.

The mixture was filtrated, and the filtrate obtained was concentrated.

To the residue, 30 parts of chloroform and 15 parts of ion-exchanged water were added, and the resultant mixture was stirred at 23° C. for 30 minutes. The mixture was separated to obtain an organic layer. The organic layer was washed with 15 parts of ion-exchanged water and this washing was further repeated three times. To the organic layer, 1.00 part of active carbon was added to stir at 23° C. for 30 minutes followed by filtration. The filtrate obtained was concentrated and the residue was mixedwith 100 parts of tert-butyl methyl ether. The mixture obtained was stirred and filtrated to obtain 6.12 parts of a salt represented by the formula (G-1), which is called as Salt (G-1).

MS (ESI(+) Spectrum): M$^+$ 263.1

MS (ESI(−) Spectrum): M$^-$ 433.1

Monomers used in Resin Synthesis Examples are following monomers (A), (B), (C), (D), (E) and (F).

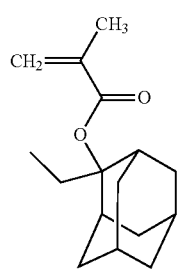

(A)

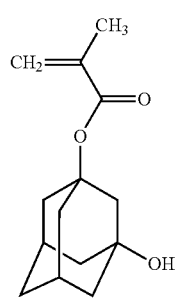

(B)

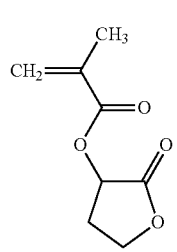

(C)

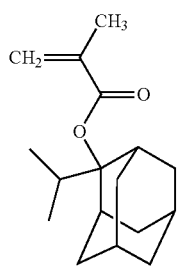

(D)

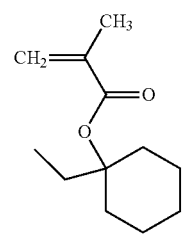

(E)

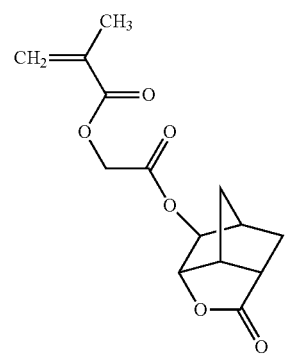

(F)

Resin Synthesis Example 1

The monomers (D), (E), (B), (C) and (F) were mixed in a molar ratio of 30/14/6/20/30 (monomer (D)/monomer (E)/monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1.00 mol % based on all monomer molar amount and azobis(2,4-dimethylvaleronitrile) as an initiator in a ratio of 3.00 mol % based on all monomer molar amount were added, and the obtained mixture was heated at 73° C. for about 5 hours. The reaction mixture obtained was poured into a mixture of a large amount of methanol and water (methanol/water weight ratio=4/1) to cause precipitation, and this operation was further repeated twice for purification. As a result, a resin having a weight-average molecular weight of about 8.1×10³ was obtained in a yield of 65%. The resin had the following structural units. This is called as resin A1.

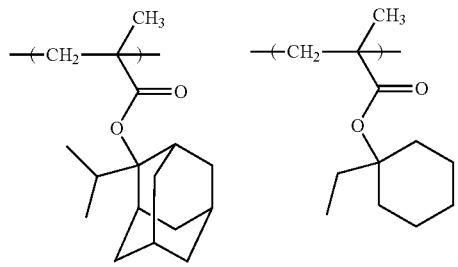

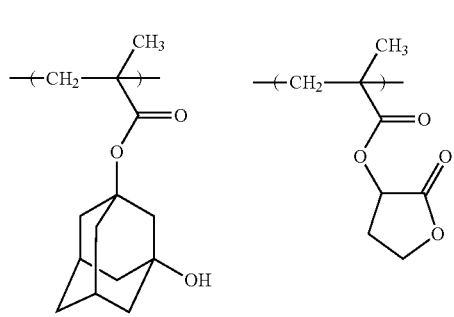

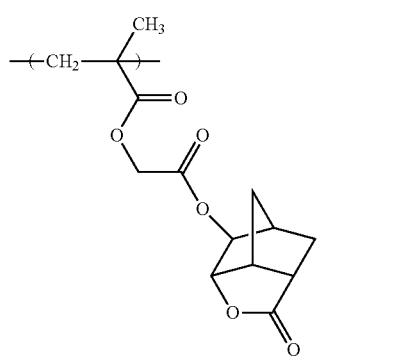

Resin Synthesis Example 2

The monomers (A), (E), (B), (C) and (F) were mixed in a molar ratio of 30/14/6/20/30 (monomer (A)/monomer (E)/monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1.00 mol % based on all monomer molar amount and azobis(2,4-dimethylvaleronitrile) as an initiator in a ratio of 3.00 mol % based on all monomer molar amount were added, and the obtained mixture was heated at 73° C. for about 5 hours. The reaction mixture obtained was poured into a mixture of a large amount of methanol and water (methanol/water weight ratio=4/1) to cause precipitation, and this operation was further repeated three times for purification. As a result, a resin having a weight-average molecular weight of about 7.8×10³ was obtained in a yield of 68%.

The resin had the following structural units. This is called as resin A2.

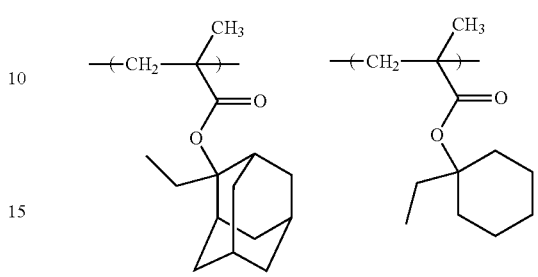

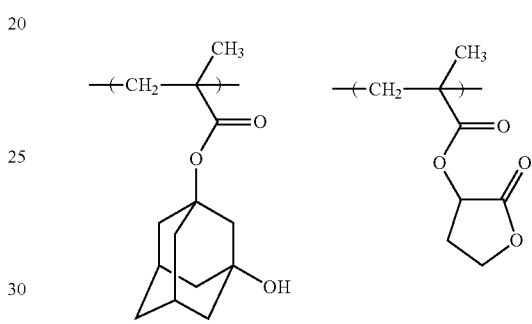

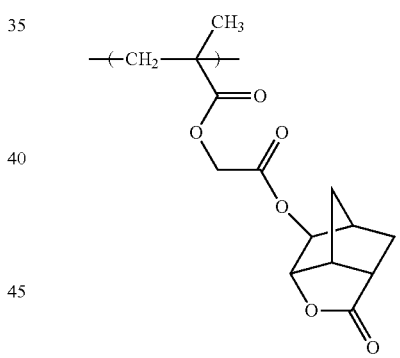

Resin Synthesis Example 3

The monomers (A), (B) and (C) were mixed in a molar ratio of 50/25/25 (monomer (A)/monomer (B)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 80° C. for about 8 hours. The reaction mixture obtained was poured into a mixture of a large amount of methanol and water (methanol/water weight ratio=4/1) to cause precipitation, and this operation was further repeated three times for purification. As a result, a resin having a weight-average molecular weight of about 9.2×10³ was obtained in a yield of 60%.

The resin had the following structural units. This is called as resin A3.

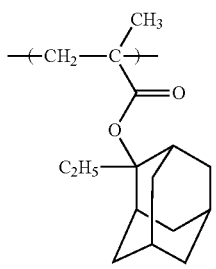
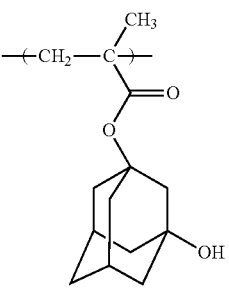
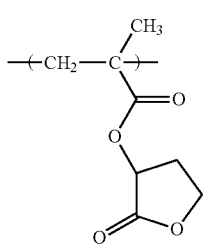

Examples 14 to 18 and Comparative Example 2

<Resin>
Resin A1, A2, A3
<Acid Generator>
Acid Generator G1: Salt (G-1)
Acid Generator B1:

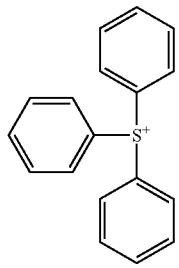
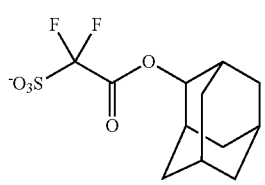

Acid Generator B2:

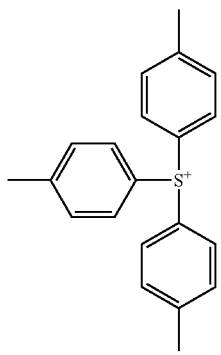

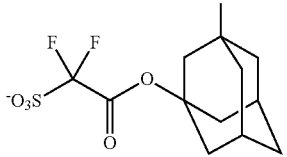

<Quencher>
C1: 2,6-diisopropylaniline
<Solvent>
Y1:

| | |
|---|---|
| propylene glycol monomethyl ether acetate | 265 parts |
| 2-heptanone | 20 parts |
| propylene glycol monomethyl ether | 20 parts |
| γ-butyrolactone | 3.5 parts |

The following components were mixed and dissolved, further, filtrated through a fluorine resin filter having pore diameter of 0.2 μm, to prepare photoresist compositions.
Resin (kind and amount are described in Table 1)
Acid generator (kind and amount are described in Table 1)
Quencher (kind and amount are described in Table 1)
Solvent Y1

TABLE 1

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 14 | A2/10 | G1/1.10 | C1/0.07 | 105 | 105 |
| Ex. 15 | A1/10 | G1/1.10 | C1/0.07 | 95 | 95 |
| Ex. 16 | A2/10 | G1/0.8 B2/0.3 | C1/0.07 | 105 | 105 |
| Ex. 17 | A2/10 | G1/0.3 B2/0.8 | C1/0.07 | 105 | 105 |
| Ex. 18 | A3/10 | G1/1.10 | C1/0.07 | 105 | 105 |
| Comp. Ex. 2 | A3/10 | B1/1.10 | C1/0.07 | 105 | 105 |

Silicon wafers having a diameter of 12 inches were each coated with "ARC-29", which is an organic anti-reflective coating composition available from Nissan Chemical Industries, Ltd., and then baked at 205° C. for 60 seconds, to form a 780 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in a column of "PB" in Table 1 for 60 seconds. Using an ArF excimer stepper for immersion exposure ("XT: 1900Gi" manufactured by ASML, NA=1.35, 3/4 Annular, X-Y polarization), each wafer thus formed with the respective resist film was subjected to line and space pattern immersion exposure, with the exposure quantity being varied stepwise.

After the exposure, each wafer was subjected to post-exposure baking on a hotplate at a temperature shown in column of "PEB" in Table 1 for 60 seconds and then to paddle development for 60 seconds with an aqueous solution of 2.38 wt % tetramethylammonium hydroxide.

Each of photoresist patterns developed on the organic anti-reflective coating substrate after the development was observed with a scanning electron microscope, the results of which are shown in Table 2.

Effective Sensitivity (ES): It is expressed as the amount of exposure that 50 nm line pattern and the space pattern become 1:1 after exposure and development.

Line Edge Roughness (LER): The photoresist pattern was observed with a scanning electron microscope, and the difference between the height of the highest point and height of the lowest point of the scabrous wall surface of the photoresist pattern was measured. When the difference is more than 3.5 nm and 4 nm or less, LER is very good and its evaluation is marked by "⊚", when the difference is more than 4 nm and 4.5 nm or less, LER is very good and its evaluation is marked by "○", and when the difference is more than 4.5 nm, LER is bad and its evaluation is marked by "x".

The smaller the difference is, the better the photopattern is.

The difference obtained was also shown in parentheses in Table 2.

TABLE 2

| Ex. No. | LER |
|---|---|
| Ex. 14 | ○ (3.86) |
| Ex. 15 | ○ (3.98) |
| Ex. 16 | ⊚ (3.48) |
| Ex. 17 | ⊚ (3.46) |
| Ex. 18 | ○ 4.42) |
| Comp. Ex. 2 | X (6.38) |

The salt of the present invention is novel and is useful as an intermediate for producing an acid generator.

What is claimed is:

1. A salt represented by the formula (I0):

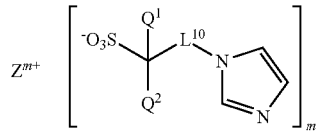

(I0)

wherein $Q^1$ and $Q^2$ each independently represent a fluorine atom or a C1-C6 perfluoroalkyl group, $L^{10}$ represents a divalent C1-C17 hydrocarbon group in which one or more —CH$_2$— can be replaced by —O— or —CO—, m represents 1 or 2, and $Z^{m+}$ represents m-valent organic or inorganic cation.

2. The salt according to claim 1, wherein m is 1.

3. The salt according to claim 1 or 2, wherein $L^{10}$ is a divalent C1-C17 saturated hydrocarbon group in which one or more —CH$_2$— can be replaced by —O— or —CO—.

4. The salt according to claim 1 or 2, wherein $L^{10}$ is —CO—.

5. The salt according to claim 1, wherein the salt represented by the formula (I0) is a salt represented by the formula (I):

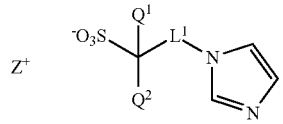

(I)

wherein $Q^1$ and $Q^2$ each independently represent a fluorine atom or a C1-C6 perfluoroalkyl group, $L^1$ represents a divalent C1-C17 saturated hydrocarbon group in which one or more —CH$_2$— can be replaced by —O— or —CO—, and $Z^+$ represents a monovalent organic or inorganic cation.

6. The salt according to claim 5, wherein $L^1$ is —CO—.

7. The salt according to claim 5 or 6, wherein $Z^+$ is a triarylsulfonium cation or an alkali metal cation.

8. The salt according to claim 5 or 6, wherein $Z^+$ is a triarylsulfonium cation.

9. A process for producing a salt represented by the formula (I):

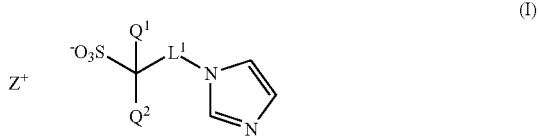

(I)

wherein $Q^1$ and $Q^2$ each independently represent a fluorine atom or a C1-C6 perfluoroalkyl group, $L^1$ represents a divalent C1-C17 saturated hydrocarbon group in which one or more —CH$_2$— can be replaced by —O— or —CO—, and $Z^+$ represents a monovalent organic or inorganic cation, which comprises reacting a salt represented by the formula (II):

(II)

wherein $Q^1$, $Q^2$, $L^1$ and $Z^+$ are the same as defined above, with carbonyldiimidazole.

10. A process for producing a salt represented by the formula (B1):

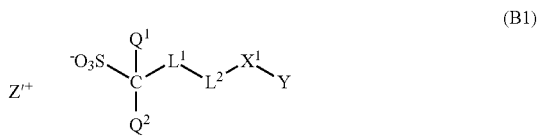

(B1)

wherein $Q^1$ and $Q^2$ each independently represent a fluorine atom or a C1-C6 perfluoroalkyl group, $L^1$ represents a divalent C1-C17 saturated hydrocarbon group in which one or more —CH$_2$— can be replaced by —O— or —CO—, $L^2$ represents —O— or —HR$^3$— in which R$^3$ represents a hydrogen atom or a C1-C4 alkyl group, $X^1$ represents a single bond or a C1-C6 alkanediyl group, Y represents a C1-C18 alkyl group which can have one or more substituents or a C3-C18 saturated cyclic hydrocarbon group which can have one or more substituents and one or more —CH$_2$— in the alkyl group and the saturated cyclic hydrocarbon group can be replaced by —O—, —SO$_2$— or —CO—, and $Z'^+$ represents a monovalent organic cation, which comprises reacting a salt represented by the formula (I'):

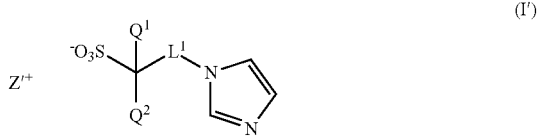

(I')

wherein $Q^1$, $Q^2$, $L^1$ and $Z'^+$ are the same as defined above, with a compound represented by the formula (IV):

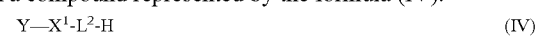

Y—X$^1$-L$^2$-H            (IV)

wherein $L^2$, $X^1$ and Y are the same as defined above.

11. The process according to claim 10, wherein $L^2$ is —O—.

* * * * *